United States Patent [19]
Cohen

[11] Patent Number: 5,439,381
[45] Date of Patent: Aug. 8, 1995

[54] DENTAL IMPLANT APPARATUS AND METHOD

[76] Inventor: Howard Cohen, 1228 Wantagh Ave., Wantagh, N.Y. 11793

[21] Appl. No.: 953,535

[22] Filed: Sep. 28, 1992

[51] Int. Cl.⁶ .................. A61C 8/00; A61C 13/12; A61C 13/225
[52] U.S. Cl. ............................. 433/173; 433/177
[58] Field of Search ............... 433/172, 173, 174, 177

[56] References Cited

U.S. PATENT DOCUMENTS

| | | |
|---|---|---|
| 4,185,383 | 2/1980 | Heimke et al. |
| 4,304,553 | 12/1981 | Heimke et al. |
| 4,406,623 | 9/1983 | Grafelmann et al. |
| 4,420,305 | 12/1983 | Linkow . |
| 4,431,416 | 2/1984 | Niznick . |
| 4,439,152 | 3/1984 | Small . |
| 4,446,579 | 5/1984 | Inamori et al. |
| 4,447,209 | 5/1984 | Sutter . |
| 4,452,776 | 6/1984 | Refojo ............................ 424/81 |
| 4,516,937 | 5/1985 | Bosker . |
| 4,661,066 | 4/1987 | Linkow et al. |
| 4,722,688 | 2/1988 | Lonca . |
| 4,744,754 | 5/1988 | Ross . |
| 4,744,755 | 5/1988 | Ross . |
| 4,758,160 | 7/1988 | Ismail . |
| 4,758,161 | 7/1988 | Niznick . |
| 4,773,858 | 9/1988 | Marquez . |
| 4,792,580 | 12/1988 | Doshi . |
| 4,832,601 | 5/1989 | Linden .......................... 433/173 |
| 4,856,994 | 8/1989 | Lazarof et al. .................. 433/173 |
| 4,960,381 | 10/1990 | Niznick . |
| 5,004,421 | 4/1991 | Lazarof ......................... 433/173 |
| 5,030,095 | 7/1991 | Niznick . |
| 5,035,619 | 7/1991 | Daftary ......................... 433/173 |
| 5,049,072 | 9/1991 | Luechen ........................ 433/173 |
| 5,062,800 | 11/1991 | Niznick . |
| 5,071,350 | 12/1991 | Niznick ......................... 433/173 |
| 5,073,110 | 12/1991 | Barbone ........................ 433/173 |
| 5,076,788 | 12/1991 | Niznick . |
| 5,114,343 | 5/1992 | Musikanti et al. ............... 433/173 |
| 5,133,662 | 7/1992 | Metcalfe . |
| 5,178,539 | 1/1993 | Peltier et al. .................. 433/173 |
| 5,211,561 | 5/1993 | Graub .......................... 433/169 |

*Primary Examiner*—Nicholas D. Lucchesi
*Attorney, Agent, or Firm*—Robert W. Fiddler

[57] ABSTRACT

A dental implant includes a healing collar that expands to a desired shape. The expandable healing collar has an orifice to permit a filler material to pass into an interior cavity between the healing collar and the base. A plurality of nested frustro-conical sections form the exterior of the healing collar which is urged upwardly by a spring and a screw. The coronal dental prosthesis that results from the expandable healing collar acts as a support for the replacement of a missing tooth so that a crown may be attached to the expanded coronal portion of the implant. This coronal extension may be angled due to its flexible telescoping mechanism and, thereafter, filled with a suitable material such as a thermoplastic resin, an epoxy-like substance or a self-gearing or light-gearing polymer. Additional apparatus and methods are described for anchoring the implant to the jawbone.

49 Claims, 20 Drawing Sheets

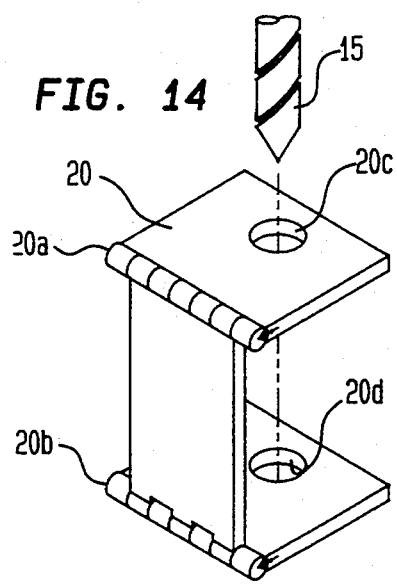
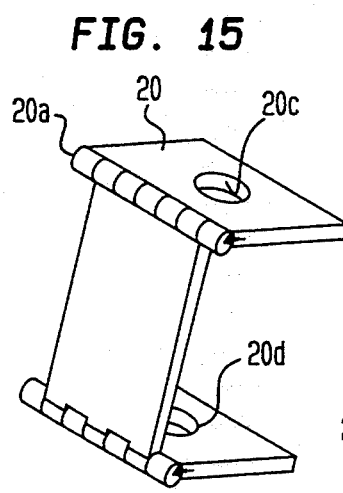
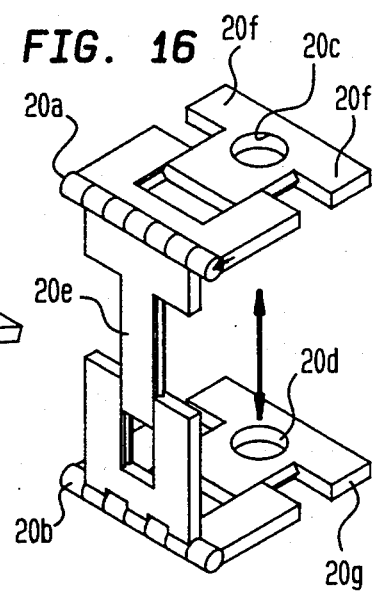
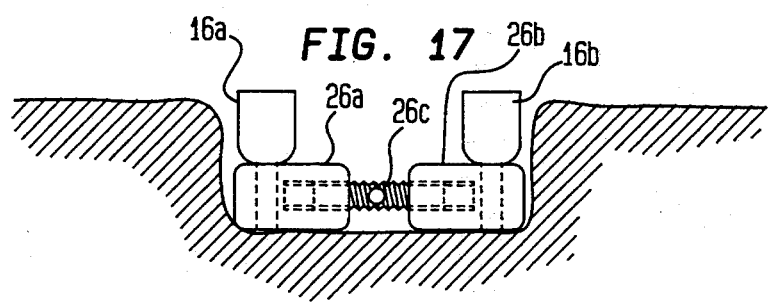
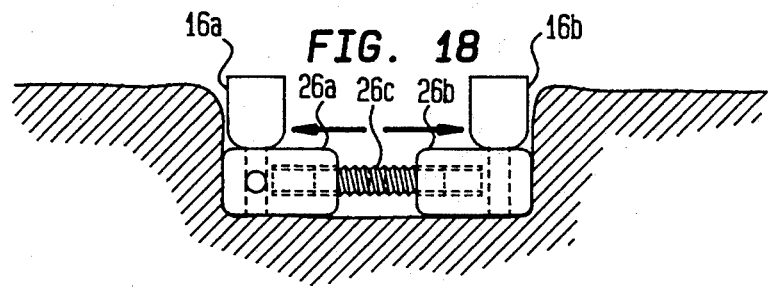
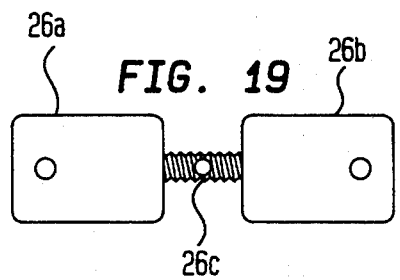
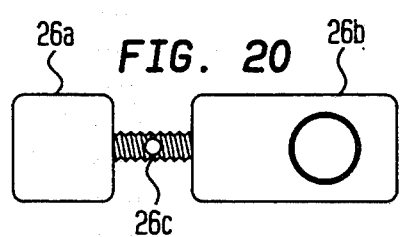
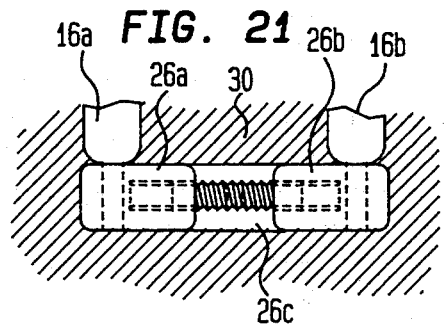

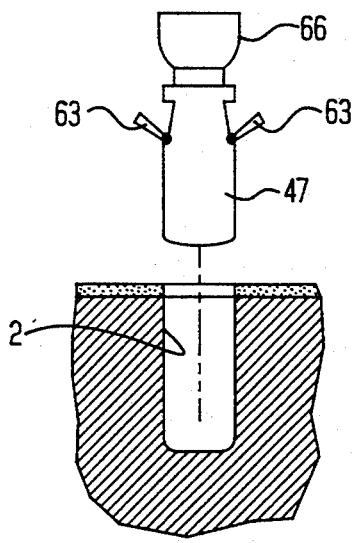
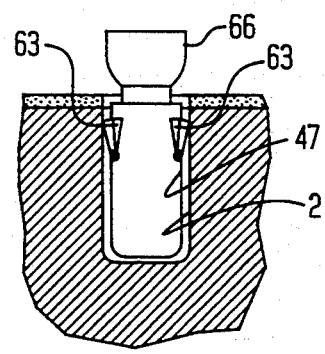
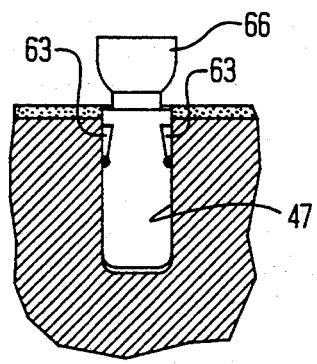
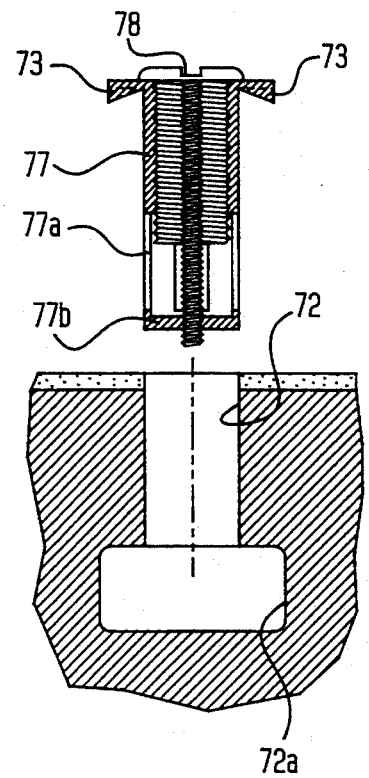
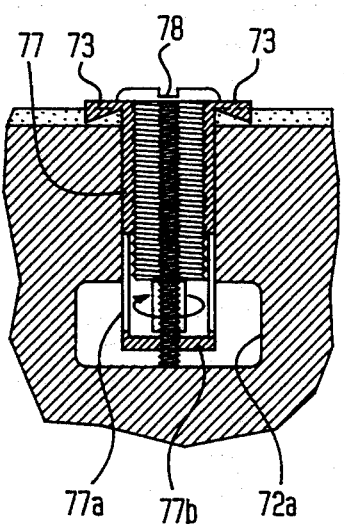
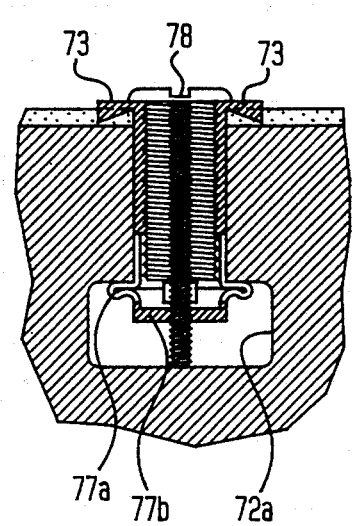

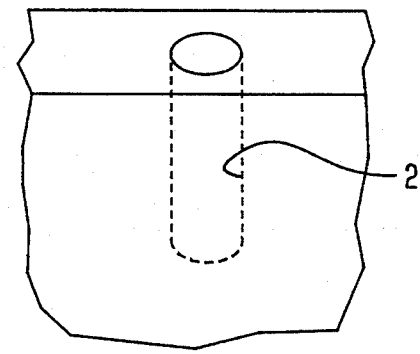

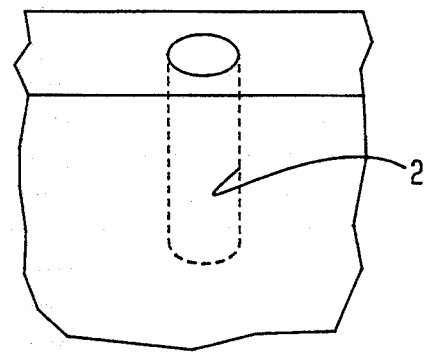

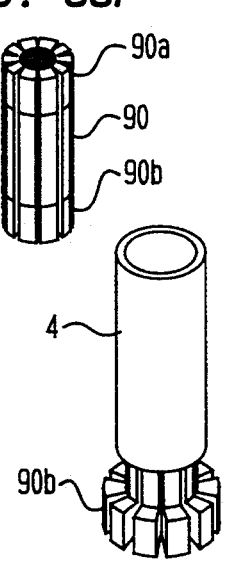

DENTAL IMPLANT APPARATUS AND METHOD

BACKGROUND OF THE INVENTION

1. Field of the Invention

The invention relates to the field of dental implants and methods for restoring a tooth.

2. Description of Related Art

Dental implants commonly employed today have many limitations. For example, there are significant potential areas for error, large inventories are required, and often the implants and techniques used are of great inconvenience to both the dentist and the patient with respect to placement and maintenance. Moreover, typical dental implants require the use of a screw to affix the coronal prosthesis to a previously located implant. The use of such screws require many difficult procedures such as removing the healing collar and affixing the coronal prosthesis to the implant, followed by an overall impression of the coronal prosthesis and the adjacent structures. The impression is then removed from the patient's mouth and the coronal prosthesis, with an attached analog which represents the vertical implant, is inserted and seated into the impression so that the dental laboratory may fabricate the restoration for the missing tooth or teeth. The dental laboratory must then send the finished product back to the dentist who again removes the healing collar and reattaches the coronal prosthesis along with the restoration made by the laboratory which is affixed to the implant by the use of a screw. Such screws have been known to fracture when chewing forces are applied rendering the restoration unsuitable. It has been attempted to place shock absorbing material between the screw and the implant so as to try to prevent the screw from fracturing. This does not always work, however, and it is normal practice to replace the shock absorbing material yearly. This is a costly procedure both in time and money to both the dentist and patient and often causes unnecessary discomfort.

The following U.S. Patents describe relevant dental implants which provide for fixed coronal prostheses: U.S. Pat. Nos. 4,431,416; 4,446,579; 4,645,453; 4,758,161; 5,030,095 and 5,071,350. However, the foregoing does not permit the coronal portion to be of various shapes and configurations such as can be achieved through the present invention.

U.S. Pat. No. 5,004,421 describes an expansion of a dental implant having some limited capabilities.

The following patents show other dental implants of various configurations that do not address the problems solved by the present invention: U.S. Pat. Nos. 4,185,383; 4,304,553; 4,406,623; 4,420,305; 4,439,152; 4,447,209; 4,516,937; 4,661,066; 4,722,688; 4,744,754; 4,744,755; 4,758,160; 4,773,858; 4,792,580; 4,960,381; 5,062,800; and 5,076,788.

SUMMARY OF THE INVENTION

Briefly described, the invention comprises a dental implant employing the use of a healing collar having a means for expansion so as to form a coronal prosthesis or attachment for a coronal prosthesis that eliminates the need for the use of screws to affix the coronal prosthesis to the internally threaded shaft of an endosseous dental implant. The expandable healing collar is made up of a plurality of nested frustro-conical sections that are sandwiched between a base and a top section. The unscrewing of a screw assisted by a spring caused the top and base to move away from each other, thereby causing an interior cavity to form as the nested frustroconical sections telescope outwardly. The interior cavity can be filled through orifices with an appropriate filler such as a thermoplastic material, an epoxy-like material, or a self-curing or light curable polymer.

A further advantage of the present invention rests in the method and preparation of the soft tissue and bone for a dental implant. This method may employ both a vertical and horizontal implant in combination to anchor the healing collar. Additionally, the invention provides means for the implant to be adjusted in situations where the bony preparation was made too large so that the implant can be held in place with a spring-like mechanism.

Accordingly, one of the principal objects of the invention is to provide improved techniques and apparatus for dental implants. A more particular object is to provide techniques and constructions which address the problems of severe bone loss so as to make the implant feasible with a more favorable prognosis. In accordance with one embodiment in the present invention, a horizontal plate is inserted into the jaw through a horizontal incision which may be precisely made with a drill, saw, or a laser, in a limiting manner so as to conserve the amount of bone removed from the jawbone.

A three-sided template is used as a guide which functions to direct and limit the removal of bone. A particular characteristic of the horizontally-directed incision is that it tends to avoid the violation of vital areas, such as the nasal sinus, nerves and blood vessel channels.

The bio-compatible horizontal plate, which may be expandable for closer adaptation to the walls of the incision, is placed in the horizontal incision forming a rigid fixture. Because the plate is expandable, the incision can be made smaller than the plate.

Once the horizontal plate has been set in place, the rigid fixation screws or wires may be applied to maintain its position. A guide, having upper and lower arms, connected by a vertical outer wall, facilitates the making of the vertical incision directly into receptacles provided for in the horizontal plate. These receptacles may be equipped with screw threads, clamps or other means of locking them into the vertical fixture. Once the vertical incision is completed and the vertical implants are screwed to the horizontal structure, all incisions are closed and the vertical and horizontal implants are left in place until osseous integration is completed in approximately 3–6 months after which the same procedure used in the prior art for vertical fixtures is employed for reconstruction in the making of the prosthesis.

Alternative techniques are disclosed for drilling incisions vertically with special drills which enable the incision to be expanded laterally. In such a case, the head of the drill is significantly larger than the shaft and the cutting takes place on the periphery of the head so as to make a cavity, which is larger in diameter at the bottom then it is at the top.

Another alternative calls for the making of an incision into the bone and using a clamp which enables the prosthesis to be held in place on the jawbone.

Other alternative embodiments of the method and apparatus will be apparent from a detailed study of the specification hereafter, with reference to the attached drawings described below.

BRIEF DESCRIPTION OF THE DRAWINGS

FIGS. 14 and 15 are perspective views of the templates of FIGS. 13A and 13B indicating how the angular orientation of the horizontal and vertical members can be varied.

FIG. 16 is a perspective view of a modified template which is vertically and laterally expandable.

FIGS. 17 and 18 are cross-sectional views illustrating an expandable modification of the horizontal implant structure of the present invention seated in an incision and in its contracted and expanded positions, respectively, so as to support two implants.

FIGS. 19 and 20 illustrate the dental implant structures of FIGS. 17 and 18 removed from the jawbone incision.

FIG. 21 is a cross-sectional vertical illustration with a modification of the implant structure of FIGS. 17 and 18 in situ including an enlarged receptacle for the lower terminal portion of two implants interposed through separate incisions at opposite ends.

FIG. 31A illustrates the vertical anchor post having spring-loaded wings about to be received in a vertical incision in the jawbone.

FIG. 31B illustrates the vertical anchor post of FIG. 31A with the wings expanded so as to fill up a large cavity and engage the sides of the vertical incision.

FIG. 31C illustrates the vertical post of FIG. 31A with the wings compressed inside a snug fit cavity.

FIG. 32A is a vertical cross-sectional illustration of a further modification of the invention in which a vertical incision is made with an enlarged base portion which is constructed to receive an internally screw-threaded sleeve, the upper portion of which has laterally-extending supporting flanges and the lower walls of which are formed of bendable metal strips and the toggle bolt structure also includes a central axial screw surrounded by an inner screw-threaded sleeve.

FIG. 32B illustrates the composite toggle bolt sleeve of FIG. 32A after it has been screwed into the vertical incision.

FIG. 32C is a vertical cross-sectional illustration of the condition of the central screw after it has been tightened, causing the lower lateral wall of the outer sleeve to draw up and bend outward like a toggle bolt and to lock the outer sleeve in place against the walls of the lower portion of the incision.

DETAILED DESCRIPTION ON THE INVENTION

During the course of this description, like numbers will be used to identify like elements according to the different views that illustrate the invention.

Figure 1:
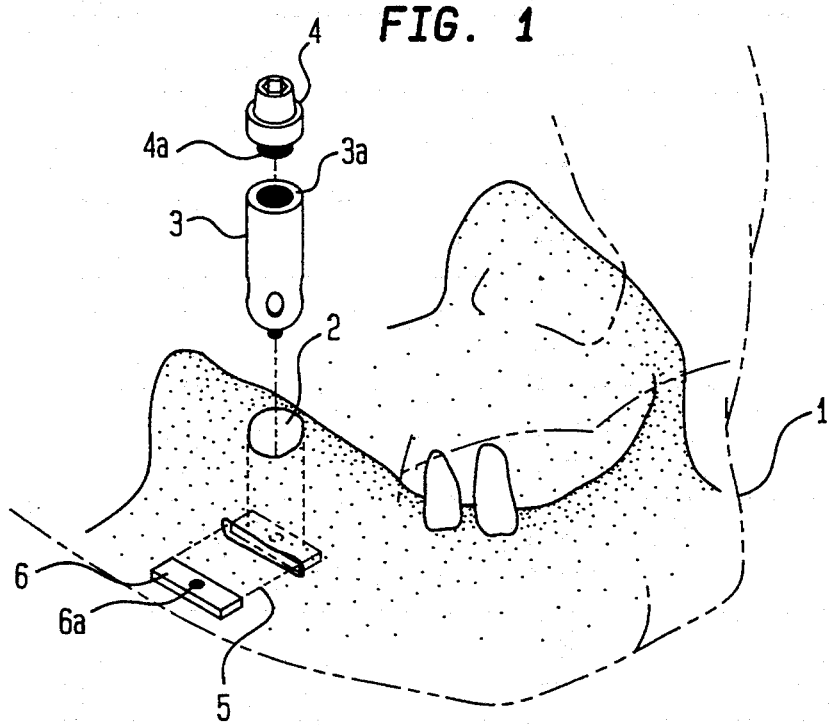
FIG. 1 is a perspective view of a patient's jaw in the process of undergoing a dental implant in accordance with one embodiment of the present invention.
Figure 2:
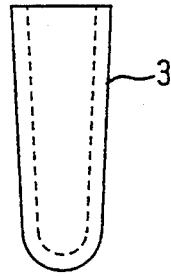
FIG. 2 is a vertical view showing a cavity in phantom of a vertical implant structure according to prior art practice.

Referring to FIG. 1, there is shown a schematic of a jaw or jawbone 1 being prepared for an implant in accordance with the present invention.

In accordance with prior art practice, a vertical incision 2 is made in the jaw 1. A sleeve 3 is interposed into the vertical incision 2. The sleeve 3 is internally screw-threaded 3a to accommodate the axially-disposed terminal 4a of the support 4 in which the prosthesis is mounted.

Figure 3:
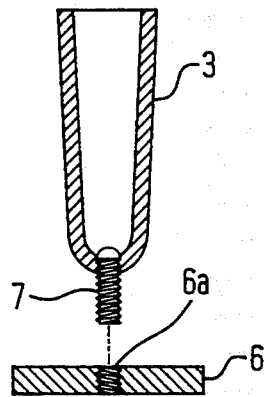
FIG. 3 is a cross-sectional vertical view of a dental implant structure including a vertical implant with accessory screw at the bottom in the process of being secured to a horizontal implant structure in accordance with one embodiment of the present invention.

In a modification of the present invention, in addition to the vertical incision 2 and the vertical support 3, a lateral incision 5 is made in a horizontal plane in jawbone 5, into which is interposed a horizontal plate 6. The use of a horizontal or oblique implant 6 in conjunction with a vertical implant 3 increases the retention of the vertical implant and allows the vertical implant to be used in areas close to vital structures such as blood vessels, nerves and sinuses. This feature will be more fully understood with reference to FIGS. 1 and 3–12. Centered in the horizontal plate 6, which being of a biocompatible material, is a screw-threaded receptacle 6a. This accommodates a screw 7 which extends vertically from the bottom of the sleeve 3, as shown in FIG. 3.

FIGS. 5, 6, 7 and 8 show different orientations of the vertical sleeve 3 and the horizontal plate 6.

Figure 4:
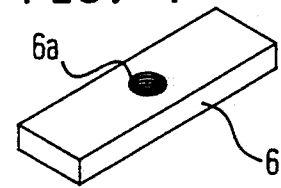
FIG. 4 is a perspective view of the horizontal implant structure of FIG. 3.
Figure 5:
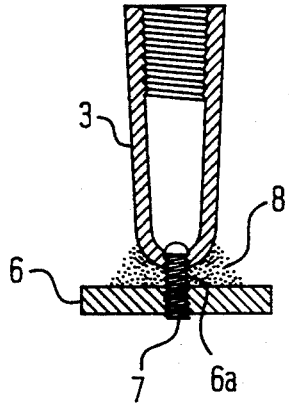
FIGS. 5, 6, 7 and 8 are cross-sectional vertical views, of various orientations of a dental implant structure in accordance with the present invention including an internally screw-threaded vertical implant and a horizontal or transverse implant fastened together with an accessory screw, such that in FIGS. 6 and 8, the bottom of the vertical structure contacts the surface of the lower structure directly, whereas in FIGS. 5 and 7, osseous material intervenes between the bottom of the vertical portion and the surface of the lower structure.

In FIG. 5, the plate 6 is interposed in a horizontal plane, with the screw 7 extending from the lower end of 3, and screwing into the screw-threaded receptacle 6a shown in FIG. 4.

Figure 6:
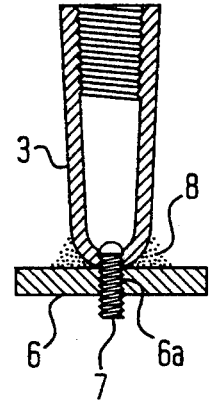

In FIG. 6, the end of the screw 7 extends beyond the lower surface of the horizontal plate 6.

Because the formation of a vertical and horizontal incision can result in a significant increase of bleeding, it may be desirable to reduce that problem. Accordingly, another embodiment of the invention comprises the use of a coating around the implant which acts to promote clotting so as to control bleeding. Another type of coating which may be used in conjunction with the aforementioned one or separately is a recombinant granulocyte colony stimulating factor (rG-CSF) such as marketed by Amgen, Inc., Thousand Oaks, Calif., under the name of Neupogen ® which helps to promote healing and to prevent infection.

Figure 7:
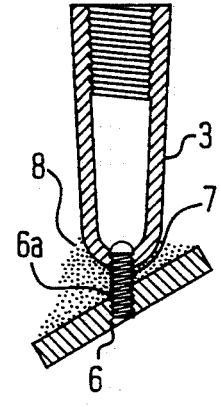

In FIG. 7, an incision is made at an angle to the horizontal, and the screw 7 is interposed vertically into the screw-threaded receptacle 6a of the angularly-disposed plate 6.

Figure 8:
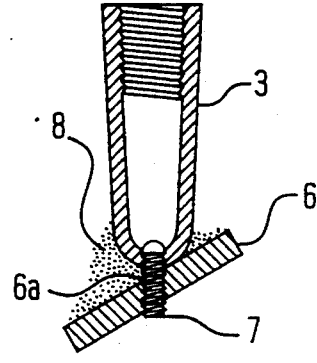

In FIG. 8, in which the plate 6 is also interposed at an angle to the horizontal, the screw 7 extends beyond the lower surface of plate 6.

As the fixtures remain in place, bony material 8 grows up in the incisions, holding the vertical support 3, and the horizontal support plate 6 in place in their respective incisions.

Figure 9:
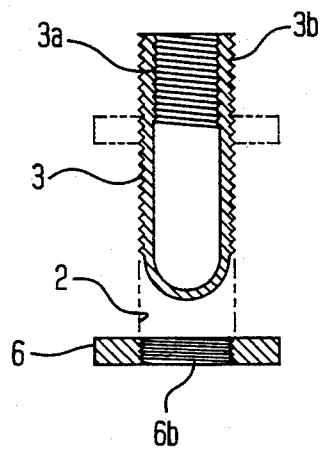
FIGS. 9 and 10 are cross-sectional views through a vertical plane of two different orientations of a modified dental implant in accordance with the present invention, including an internally and externally screw-threaded vertical implant in the process of being interposed into the screw-threaded receptacle of a horizontal or transversely disposed implant.
Figure 10:
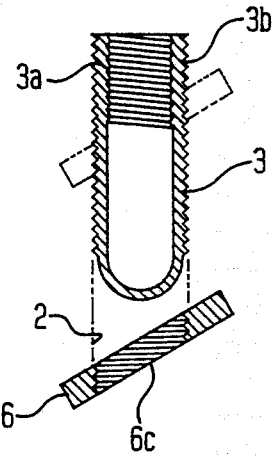

FIGS. 9 and 10 show another modification of the structure of the present invention in which the vertical support sleeve 3 of FIGS. 1–8 is screw-threaded both externally, 3b and internally, 3a.

The plate 6 shown in FIGS. 9 and 10 is interposed into a vertical incision 2. Plate 6 has an internally screw-threaded receptacle 6b in the plate, in each case, and is dimensioned to accommodate the external screw threads 3b of the sleeve 3. FIG. 10 shows a plate 6 disposed at an angle to the horizontal plane, the central internally screw-threaded receptacle 6c being dimensioned to accommodate the vertical sleeve or support 3b on a plane transverse to the horizontal.

Figure 11:
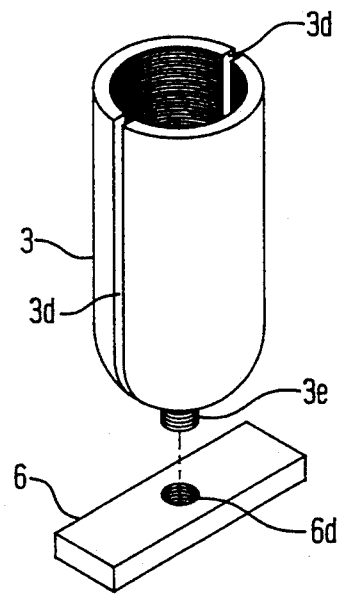
FIG. 11 is a perspective view of a modification of a combination of FIGS. 9 and 10 in which the vertical implant structure is bifurcated for expansion purposes, and terminates at its bottom end in a screw projection which is accommodated and received in a screw-threaded receptacle in the horizontal plate.

FIG. 11 shows a further modification of the vertical sleeve 3 in accordance with the present invention in which the internally screw-threaded sleeve 3 is split lengthwise by a pair of diametrical slits 3d which are constructed to open up, or close up to enable the sleeve 3 to fit into the vertical incision 2. The sleeve 3 terminates at its bottom in an externally screw-threaded fitting 3e which is constructed to fit into the internally screw-threaded receptacle 6d of the plate 6 interposed in a horizontal incision.

Figure 12:
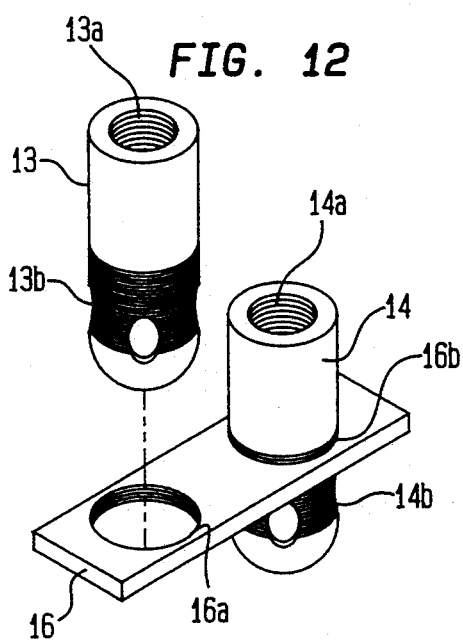
FIG. 12 illustrates in perspective view another modification of the present invention in which the horizontal implant structure has screw-threaded receptacles for two vertical implant structures which are internally and externally screw-threaded.

FIG. 12 shows a modification of the invention in which a single horizontal plate 16 has two internally screw-threaded receptacles 16a and 16b aligned side by side accommodating two vertical externally-threaded sleeves 13 and 14.

One major difficulty associated with prior art bony preparation is the proper angulation of the drill through the jaw. This technique is often performed according to the eye and skill of the dental surgeon, however, it is subject to a significant amount of error. In order to minimize the error problem, an alternative embodiment set forth in FIGS. 13A–16 below call for an adjustable template 20 which permit vertical and horizontal incisions to be made and properly located so that vertical and horizontal implants can be properly placed.

Figure 13A:
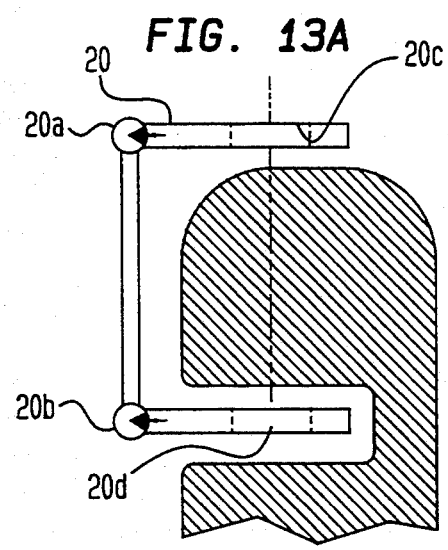
FIGS. 13A and 13B are vertical cross-sectional elevations showing in two different angular orientations the use of templates which are utilized as guides for the purpose of properly placing and aligning the vertical incision relative to the screw-threaded receptacles in the horizontal implant structure.

FIG. 13A shows, in vertical section being interposed into the jaw through a horizontal incision, a template 20 having three intersecting legs hinged at the intersections 20a and 20b. Centered in the top leg which is disposed parallel to the top of the jaw, is an opening 20c which is aligned with an opening 20d in the lower leg for receiving and vertically aligning the drill.

Figure 13C:
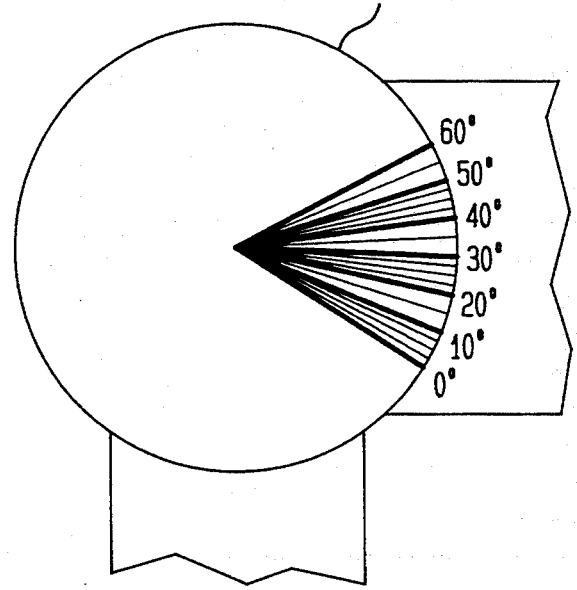
FIG. 13C is a top plan view of the templates of FIGS. 13A and 13B showing a scale to determine the proper angular orientation.
Figure 13B:
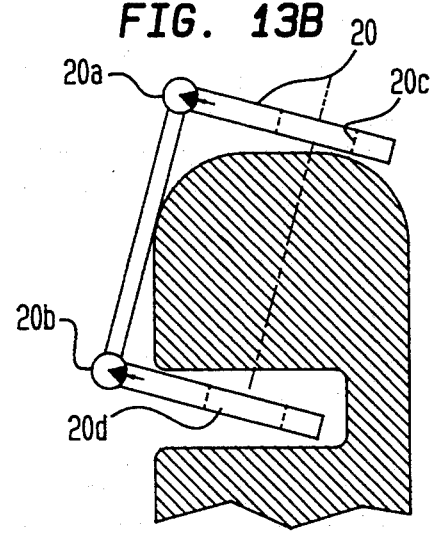

FIG. 13B shows the template 20 being interposed at an angle to the horizontal incision.

FIG. 13C is a top view of template 20 showing how the angular position of 20 is set. FIG. 13C is a view looking down on the template of FIGS. 13A and 13B, showing how the template can be rotated to change its angle in the horizontal plane to fit into the incision from a desired angle.

FIGS. 13 and 15 show, in perspective, in several orientations, the metal templates 20, which function as guides for a vertical drill 15, which is interposed into a vertical incision to enable the drill 15 to drill an opening in the horizontal or transverse plate 59 the horizontal incision at the lower level which is aligned with the vertical incision interposed into the upper level of the jaw. It is apparent that legs of the three-legged template 20 is hinged, as shown in FIGS. 14, 15 and 16, so that it can be moved in the vertical incision to position the lower bore 20d in the desired position, aligned with the upper bore 20c.

FIG. 16 shows a template similar to that shown in FIGS. 14 and 15, and having adjustable top and bottom panels, 20f and 20g each having a slidable central panel, which enable the height and width of the template 20 to be adjusted as needed to fit into and fill up the incision.

FIGS. 17 and 18 show in vertical section an incision in the top of the jaw in which expandable plate 26a–26b is interposed into the incision. The two plate sections 26a, 26b are coplanar and are joined on a lateral plane by a screw 26c which enables the gap between them to be opened or closed. Plates 26a–26b are interposed in the incision in parallel-plane relation, so that screw 26c allows the relation between plates 26a and 26b to expand or contract. A hole in screw 26c allows for expansion or contraction of the screw. The vertical sleeves 16a and 16b each terminate at their respective bottoms in a projecting screw, as shown in FIG. 11, which fits into a screw-threaded receptacle centered in a respective one of the horizontal plates 26a and 26b The purpose of the expandable embodiment illustrated in FIGS. 17–21 is to reduce failures of blade-like implants when bony incision is made improperly.

FIG. 17 shows the combination in retracted relation in the incision; whereas FIG. 18 shows the combination in expanded relation, so that the incision is substantially filled.

FIGS. 19 and 20 are views from the top of the expandable plates 26a and 26b which are removed from the incision.

FIG. 21 shows the expandable plates 26a–26b installed in the gum in which the bone has been allowed to grow up between the sleeves 16a, 16b holding them in place to support two prostheses.

Figure 22:
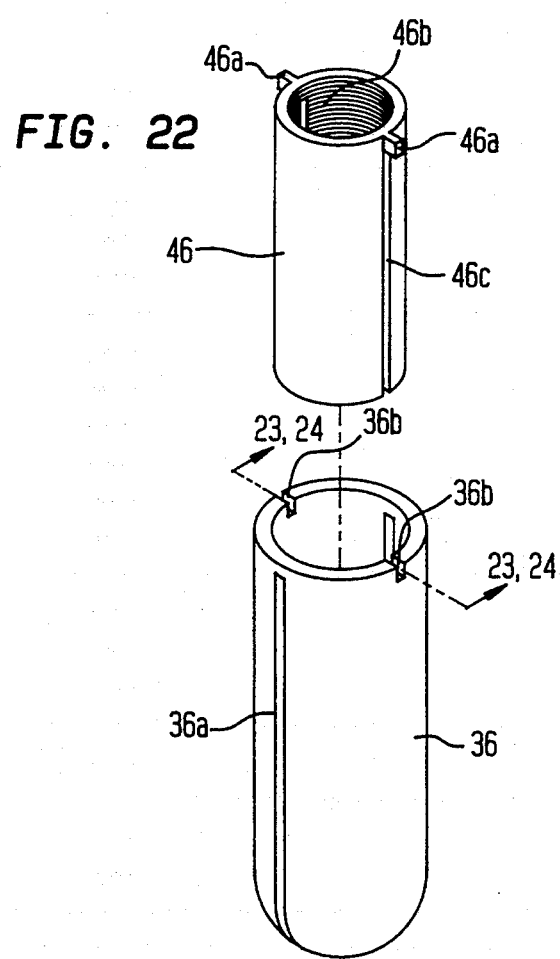
FIG. 22 is a perspective view with the top removed of a two-part insert having a cylindrical expansible sleeve with an inner member fitting into the sleeve telescopically, and internally screw-threaded to accommodate an axially disposed screw which supports the vertical implant.

FIG. 22 shows in perspective view another modification of the invention in which the cylindrical vertical support comprises an outer sleeve 36 and an inner sleeve 46 which is designed to fit telescopically into the outer sleeve 36. The cylindrical inner sleeve 46 is open at both ends, and is screw-threaded internally 46b, and has a pair of projecting bosses or wings 46a diametrically disposed at its upper end. Extending vertically downward to the bottom of sleeve 46 are a pair of longitudinal slits 46c.

The bosses or wings 46a are designed to seat in a pair of diametrically-disposed slots 36b notched into the top rim of the outer sleeve 36, which terminates at the bottom in a closed, rounded end. On opposite sides of the outer sleeve 36 are a pair of slits 36a, extending from just below the top to the bottom, which are in a plane normal to the plane of the notches 36b.

Figure 23:
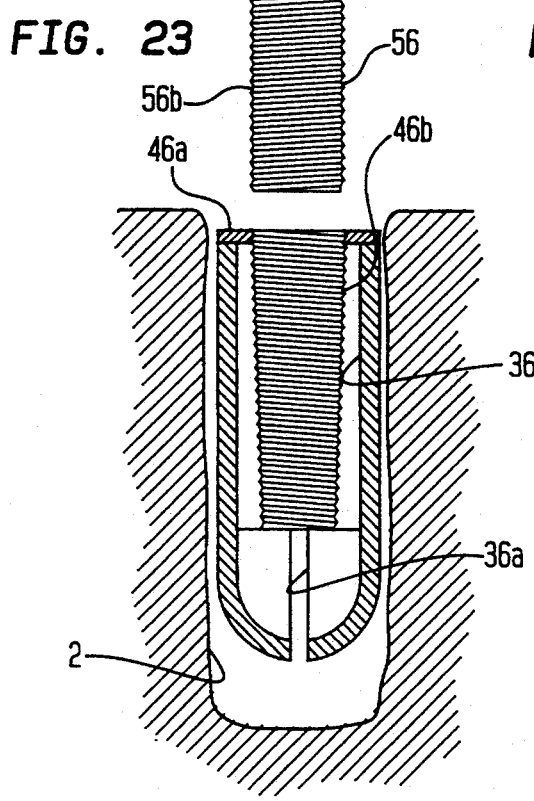
FIGS. 23 and 24 are vertical cross-sectional illustrations of the device illustrated in FIG. 22 installed in a vertical incision where the diameter of the internal member becomes smaller as the depth is increased, causing the insert to spread in the incision.
Figure 24:
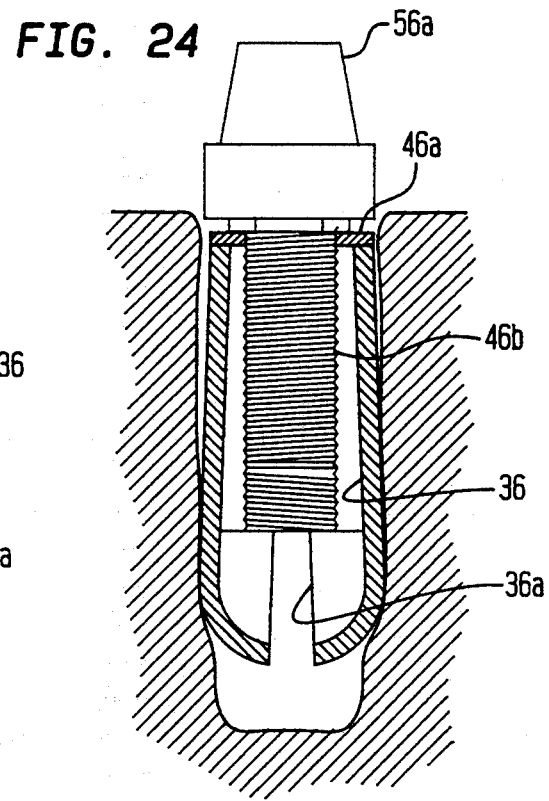

FIGS. 23 and 24 are vertical sections through the jaw showing the combination of FIG. 22 being put into place in an incision 2, in FIG. 23, and screwed into place and expanded in FIG. 24.

The vertical support member 56 has a top portion 56a which represents an expanded healing collar, shown in FIG. 23, which is designed to support the prosthesis, has a screw-threaded stem 56b which extends down vertically and is accommodated in the screw-threaded interior 46b of the inner sleeve 46. In FIG. 24, the slit 36a of outer sleeve 36 is initially partially closed, and opens up a support member 56 is screwed into place vertically, tending to fill up the incision 2.

Another modification of the invention is shown in FIGS. 25A, 25B, 26A, 26B, 27A and 27B in which a thin lining of compressible elastomer material, 71, such as, for example, polyurethane, aerogel, or other compressible polymers well-known in the art, is interposed between the inner and outer sleeves 47 and 36, respectively. In each of the foregoing, the elastomer coating 71 between the inner and outer sleeve 47 and 36, respectively, is in a slightly different position.

One problem associated with the prior art is the difficulty of absorbing shock imparted to the crown and transmitted to the implant. Shock can cause the crown and/or implant to break or dislodge. One prior art technique to deal with the problem of shock associated with dental implants is described in U.S. Pat. No. 4,452,776. However, an improved technique is described herein. According to one embodiment illustrated in FIGS. 25A–27B, a compressible material is located between the inner and outer wall of the vertical implant so as to act as a shock absorber when excessive forces are applied. Alternatively, as described in FIGS. 40A–40D, a spring can be employed to absorb some of the shock or an elastomer material can be located at the top of the implant between the implant and the healing collar and/or prosthesis.

Figure 25A:
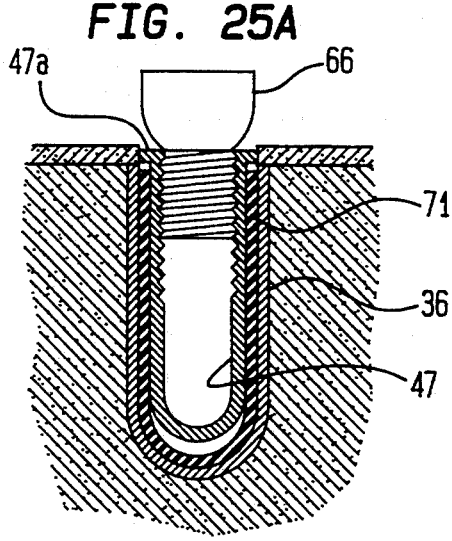
FIGS. 25A and 25B, 26A and 26B, 27A and 27B illustrates modifications of the vertical implant structure of FIG. 23, et seq., in vertical cross-sectional detail comprising an inner and outer sleeve including an elastomer containing material such as aerogel, polyurethane, or a compressible polymer, in various areas, and between the inner and outer sleeves.
Figure 25B:
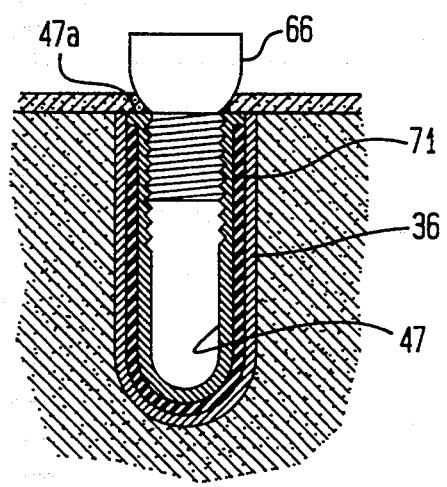

In FIG. 25A, the inner sleeve 47 is interposed into the incision so that the diametrical projections 47a are level with the top layer of the gum. When the stem of support 66 is screwed into inner sleeve 47, the bottom of inner sleeve 47 does not reach quite to the bottom of the incision. In FIG. 25B, the prosthesis support 66 rests on the upper gum line, and the diametrical projections 47a are located just below the gum line, sealing in the layer 71 of elastomer. the stem 47 of 66 is screwed all the way into the inner sleeve so that the combination fills up the incision.

Figure 26A:
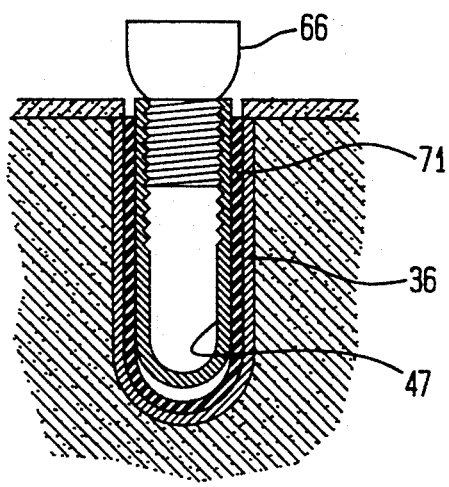

In FIG. 26A, the outer sleeve 36 is interposed into the vertical incision, so that it extends to the bottom. The elastomer layer 71 is put in place forming an inner lining of sleeve 36. The stem 47 of support 66, which has no projections at the gum surface, is screwed into place, extending nearly to the bottom of the incision. Thus, the annular top edge of the elastomer layer 71 is exposed to the air.

Figure 26B:
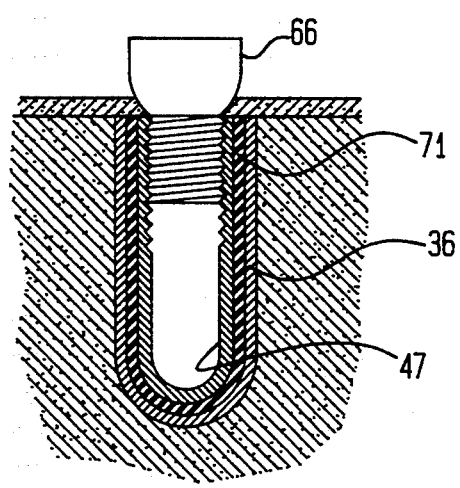

In FIG. 26B, the top edge of the elastomer layer 71 is below the gum line, so that it is sealed in and not exposed to the air. The stem 47 of support 66 is screwed to the bottom of the incision in contact with the elastomer lining.

Figure 27A:
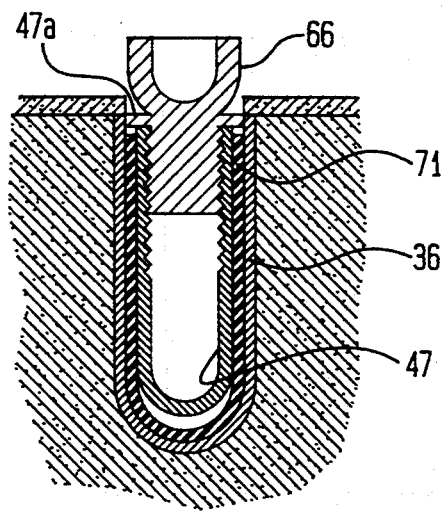
Figure 27B:
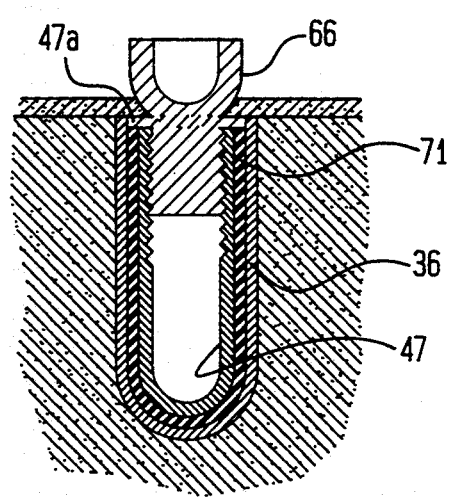

FIGS. 27A and 27B show other modifications in which the support 66 has diametrical projections 47a. When the inner stem 47 is screwed into the incision, almost to the bottom, the projections 47a close up the opening slightly below the gum level sealing in the elastomer layer 71. In 27B, when the stem 47 is screwed into the bottom of the incision in contact with the elastomer layer 71, the support 66 is embedded in the gum and the projections 47a close off the incision below the level of the gum.

The present invention also provides a means for the implant to be adjusted in situations where the incision made during the bony preparation was too large. A similar problem is addressed in U.S. Pat. No. 5,030,095 but not as extensively or effectively as the modification described in FIGS. 28-36C.

Figure 28:
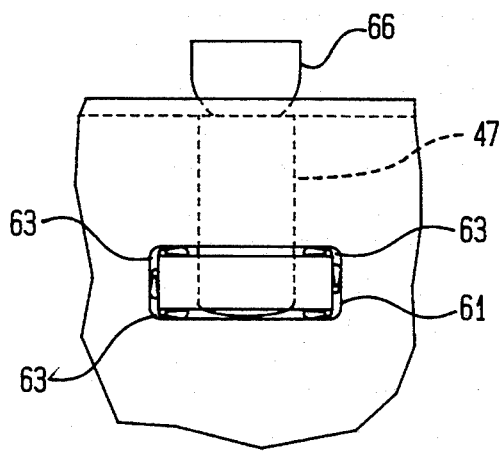
FIG. 28 illustrates an expandable horizontal anchor plate including spring-loaded wings which are compressed to fit within a horizontal cavity in the jawbone.
Figure 29:
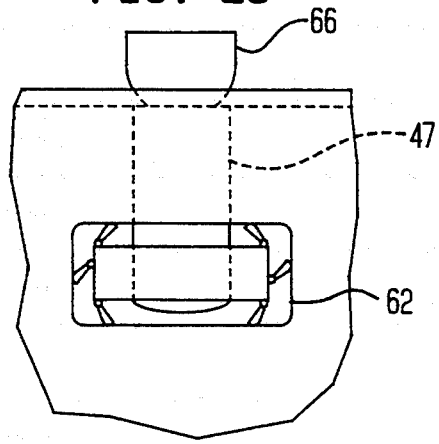
FIG. 29 illustrates the embodiment shown in FIG. 28 with the spring-loaded wings expanded to fill up a larger cavity.

FIGS. 28 and 29, show further modifications of the invention 61, in which the screw-threaded stem 47 of the support 66 extends vertically and is rooted in a horizontal incision in the jaw, resting in an expanded chamber 62 which is the correct size to accommodate and hold in place the lower end of the stem 47 which rests in the horizontal incision 61.

Figure 30A:
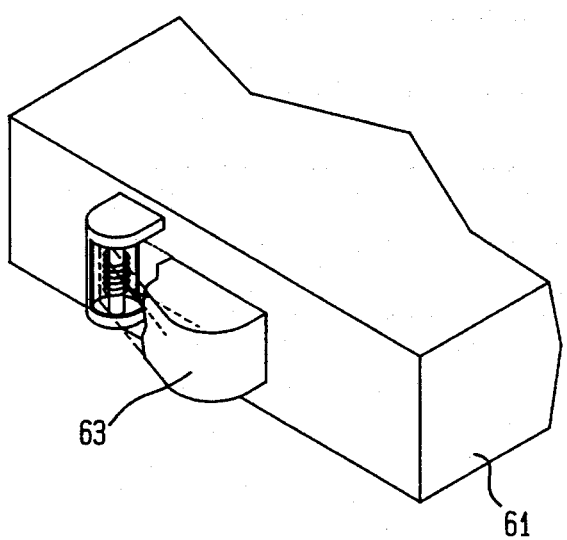
FIG. 30A is a detail of the wing structure illustrated in FIGS. 28 and 29 with the wing expanded outside of the anchor plate.
Figure 30B:
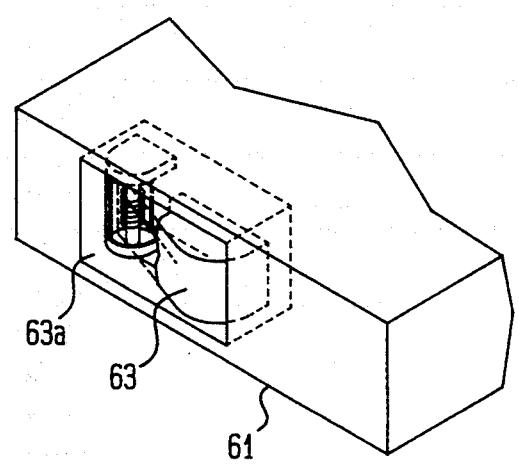
FIG. 30B illustrates the wing structure of FIGS. 28 and 29 with the wing compressed inside the horizontal anchor plate.

A special feature of this embodiment is a plurality of small leaf-like springs or wings 63 which are connected around the periphery of the metallic rectangular base support 63, which is shown removed from the incision 2 in FIGS. 30A and 30B. The springs or wings are housed in a recess 63a in the lateral wall of the rectangular container 61. FIG. 30A shows one of the wings 63 released outwardly to hold 61 in place in the lower incision 62 if the incision is larger than 61. FIG. 30B shows the wings 63 retracted into recess 63a, in the case in which the rectangular base member 61 fits into the incision 62.

FIGS. 31A, 31B and 31C illustrate the use of wings or springs 63, which are of the form shown in FIGS. 31A, 31B on the body 47 of the vertical support member 66.

FIG. 31A shows the support member 66 with the wing or spring members 63 on the stem 47, in open position, being lowered into the vertical incision 2. FIG. 31B shows the support 66 and stem 47 in place in an oversized incision 2 with the springs or wings 63 in expanded position so as to hold 66 in place in the oversized incision 2. FIG. 31C shows support 66 and its stem 47 in place in an incision 2 which is of the desired size, whereupon the wings or spring 63 are retracted into recesses in the stem 47, in the manner shown in FIG. 31B.

FIGS. 31A, 32B, and 32C show another embodiment of the present invention, in which a vertical incision 72 has been made which terminates at the bottom in an expanded horizontal incision 72a.

Referring to FIG. 32A, a composite metal sleeve 77 is internally screw-threaded and has a pair of wings or springs 73 which extend out horizontally from its upper lip. The lower end of metal sleeve 77 terminates in a pair of linear supporting strips 77a which project downward from the walls of sleeve 77. The supporting strips 77a may comprise, for example, a soft, biocompatible material such as a plastic, ceramic or titanium or titanium alloy and/or any combination of the above. The lower ends of strips 77a are anchored in a collar 77b.

An inner screw 78 is interposed in the screw-threaded interior of sleeve 77, which is adapted to be screwed down vertically in axial relation to the sleeve 77, extending at its lower end through a screw-hole centered in collar 77b.

FIG. 32B shows sleeve 77 interposed into the vertical incision 72, and extending into the expanded chamber 72a, with the bottom of screw 78 being extended beyond the collar 77b to the lower periphery of incision 72a. As the screw 78 continues to be rotated in a clockwise direction so that the lower end extends beyond the collar 77b, the soft metal strips 77a bend upwardly and outwardly against the upper periphery of the horizontal chamber 72a, fastening the sleeve 77 in place at the top and bottom of vertical incision 72.

Figure 33A:
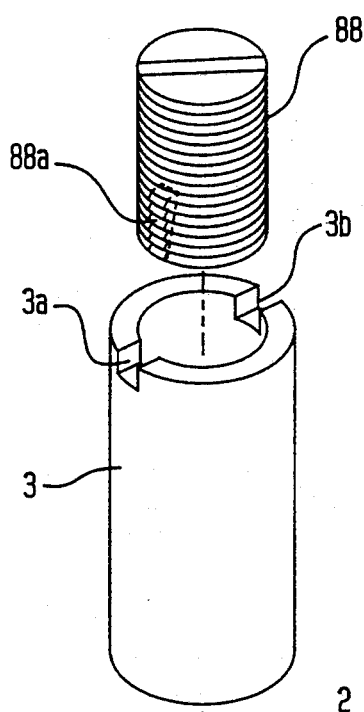
FIG. 33A illustrates in a perspective elevation, a vertical incision constructed to accommodate an internally screw-threaded outer sleeve notched at the top which in turn accommodates an internal screw such that the apparatus has near at its bottom end a plurality of spring-biased toggle wings which bend outwardly as the central member is screwed into place.
Figure 33B:
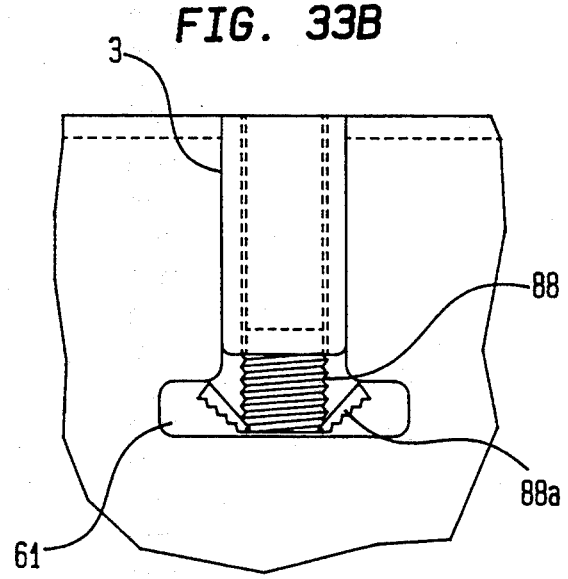
FIGS. 33B and 33C illustrate in vertical cross-sectional views the central screw in place, with the spring-loaded wings bent outwardly to hold the implant in place in the lower portion of the incision.
Figure 33C:
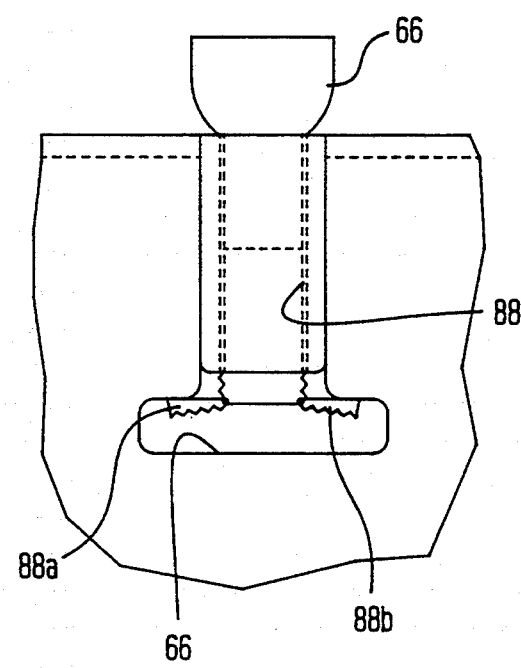

A further modification of the invention is shown in FIGS. 33A, 33B and 33C. The metal sleeve 3, open at both ends, which is designed to be accommodated in the incision 2, has a pair of diametrically-disposed notches 3a and 3b on its top edge. Sleeve 3 is internally screw-threaded to accommodate the internal screw-threaded member 88 which is equipped near opposite lower edges with a pair of spring-biased wings 88a.

When the member 88 is screwed into place in the internal screw threads of the outer sleeve 3 until it contacts the bottom of the horizontal incision 61, the wings or springs 88a bend outwardly.

In order to tighten the member 88 in the incision 2, member 88 is screwed in the reverse direction, counter-clockwise, so that the spring biased wings 88a, 88b abut against the roof of the horizontal incision 61, holding the stem of 66 in place in the vertical incision 2.

Figure 34:
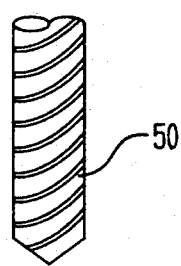
FIG. 34 illustrates a prior art drill for drilling a vertical incision.

FIG. 34 shows the prior art mechanism for drilling the vertical incision 2 from the top of the gum using a conventional drill 50.

Figure 35A:
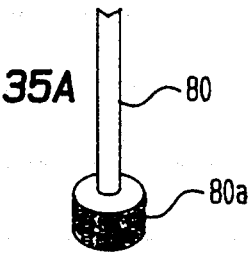
FIG. 35A illustrates a modification of the drill of FIG. 34 in which the diameter of the head of the drill is larger than the diameter of the shaft of the drill and includes a cutting surface on its periphery.
Figure 35B:
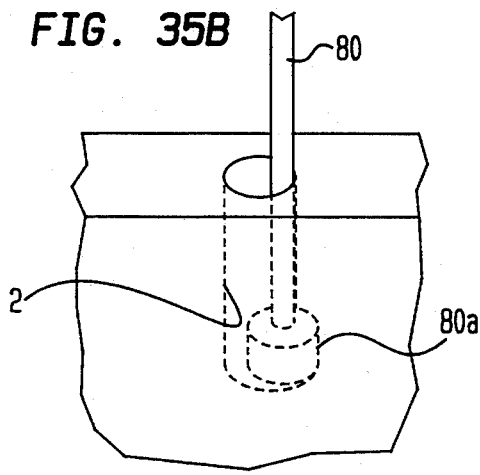
FIGS. 35B and 35C illustrates the manner in which the drill of FIG. 35A produces an incision which is larger at the bottom than it is at the top.
Figure 35C:
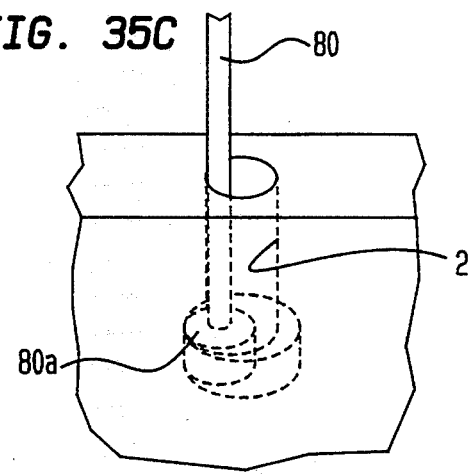

Prior art efforts to drill into the jawbone and prepare a site for reception of an implant are described in the prior art in patents such as U.S. Pat. No. 4,431,416. It is difficult, however, to provide a decent base for an implant so that it does not slip out of its incision. In order to avoid this problem, another embodiment of the invention resides in the method of the use of a special drill which has means for cutting on its edges as illustrated in FIGS. 35A-35C. Such a drill is desired when it is necessary to use a small implant and additional means for retention of said implant is desired without deepening the vertical incision. According to this embodiment, a vertical bony incision is made in the usual manner with a prior art drill such as illustrated in FIG. 34. Then the special drill 28 with a special cutting edge having a cutting surface on its periphery 80A is passed down the incision and manipulated in the manner illustrated in FIGS. 35B and 35C. This allows for the placement of a vertical implant such as illustrated in FIGS. 32A, 32B, 32C, 33A, 33B, 33C, 35E, 35F 36A, 36B and 36C which include means for locking into the enlarged bony prepared site. This technique is described in further detail below.

Figure 35D:
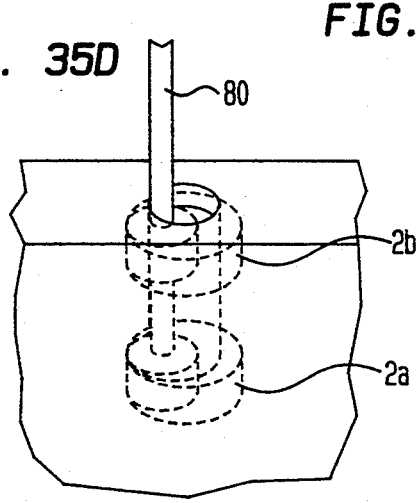
FIG. 35D illustrates a modification of the drill illustrated in FIG. 35A which includes an upper and lower cutting surface for producing two relatively enlarged horizontal incisions in the jawbone.

In accordance with the present invention, the vertical incision 2 can be enlarged at any level through its length by the use of a modified drill 80, as shown in FIG. 35A, having an enlarged cylindrical drill head 80a. This may be manipulated in the vertical incision 2, as shown in FIGS. 35B, 35C and 35D, to make enlarged horizontal cavities, extending out from the vertical cavity 2, such as 2a and 2b, at any desired level.

Figure 35E:
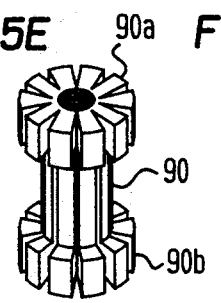
FIG. 35E illustrates a vertical post having multiple splits so that it is compressible and can fit into a sleeve which is received in the vertical incision drilled into jawbone.
Figure 35F:
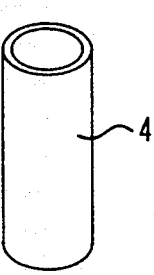
FIG. 35F illustrates the manner in which the vertical post can be compressed and the manner in which the vertical post expands once it escapes from the bottom of the sleeve.

FIGS. 35E and 35F illustrate the use of an expandable implant 90 which when compressed fits inside of sleeve 4. The expandable implant 90 is shown in its expanded state in FIG. 35E prior to insertion into sleeve 4. It includes an expandable head section 90a and bottom section 90b which would fit respectively well into the top and bottom sections 2b and 2a of the vertical cavity illustrated in FIG. 35D. The expandable implant 90 can be compressed to the size shown at the top of FIG. 35F so that it will slide through the top of sleeve 4. Sleeve 4 guides it through the vertical incision 2 so that the bottom section 90b can expand into the bottom section 2a of the incision shown in FIG. 35D and, after sleeve 4 is completely removed, the top section 90a will also expand into its respective cavity 2b.

Figure 36A:
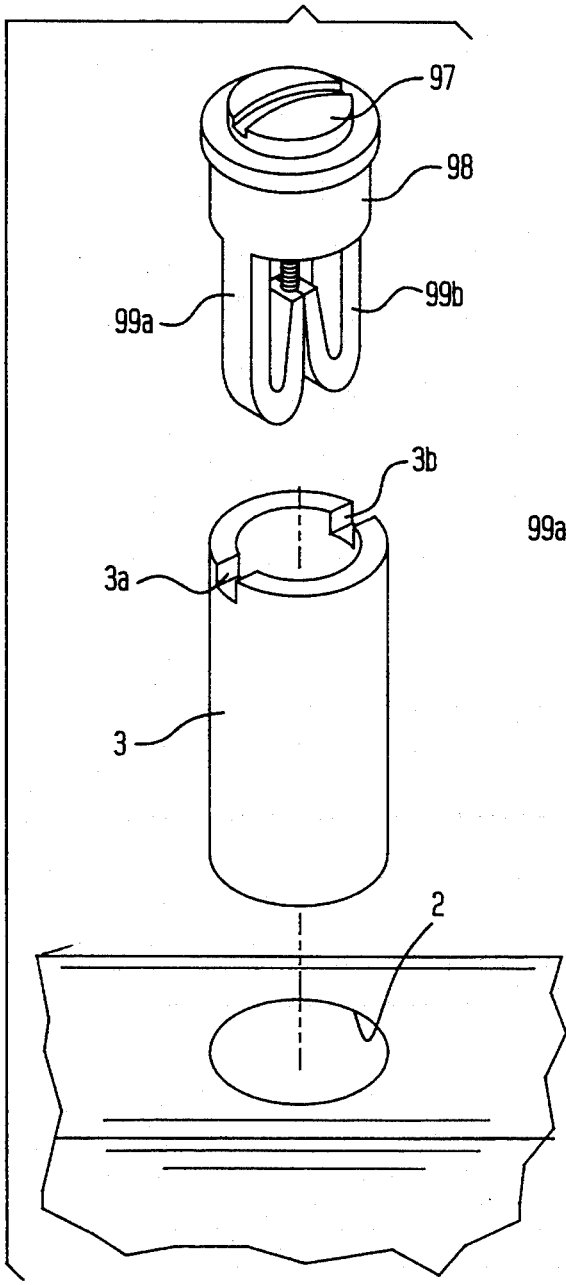
FIG. 36A illustrates in a perspective vertical fashion, a modification of the implant of FIG. 33A which is constructed to be received telescopically in a cylindrical sleeve which is notched at the top and which is accommodated in a vertical incision such that when the prosthesis support is lowered into the vertical incision, the lower end of the internal screw portion is bent inwardly and upwardly, but is constructed to spread laterally into the lower portion of the incision and flattened against the inner walls of the lower portion of the incision as the support for the prosthesis is tightened into place, as shown in FIGS. 36B and 36C.
Figure 36B:
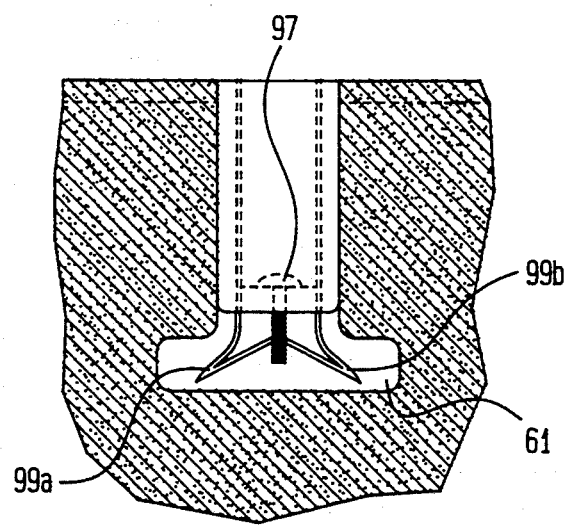
Figure 36C:
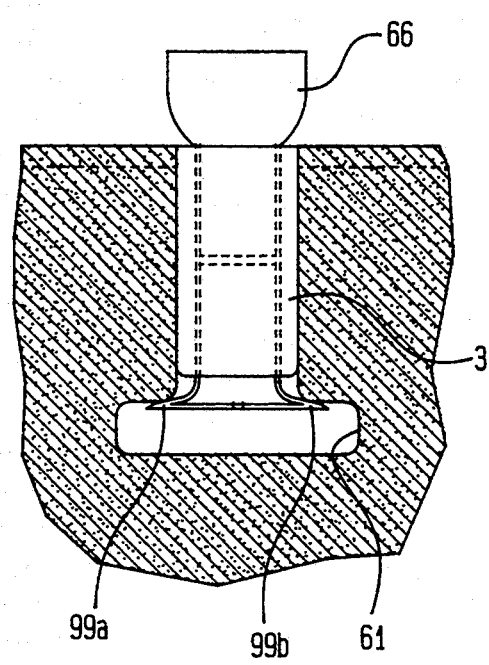

A further modification of the invention is shown in FIGS. 36A, 36B and 36C. This comprises an outer metal sleeve 3, which is designed to be interposed in a vertical incision 2, similar to that shown in FIG. 34A and having diametrical notches 3a and 3b, in its upper annular end.

An internal member 98 which fits telescopically into the sleeve 3, has a cylindrical top and terminates at its lower end in a pair of spring-biased metal wings or legs 99a and 99b. an axial screw 97 passes between wings or legs 99a and 99b, and is screwed down until 99a and 99b are expanded in opposite directions into the lower horizontal incision 61 as shown in FIG. 36B.

As shown in FIG. 36C, as the axial screw 97 is drawn back up, the wings or legs 99a and 99b being of soft metal, are caused to bend outward, securing the sleeve 3 in place against the roof of the horizontal incision 61. the sleeve 3 serves as a support for the prosthesis 66 at the gum line.

A still further embodiment of the invention described in FIGS. 27A–27C and FIGS. 39A–39B provides for the attachment of an implant in areas where there is very little bone. The implant is in the nature of a strap attached to an expandable healing collar. The adjustable strap may go through a small incision in the bone or completely around the bone where, for example, there might be severe atrophy of the bone of the mandible. Such an implant requires very little bony preparation so as to preserve the remaining existing bone.

Figure 37A:
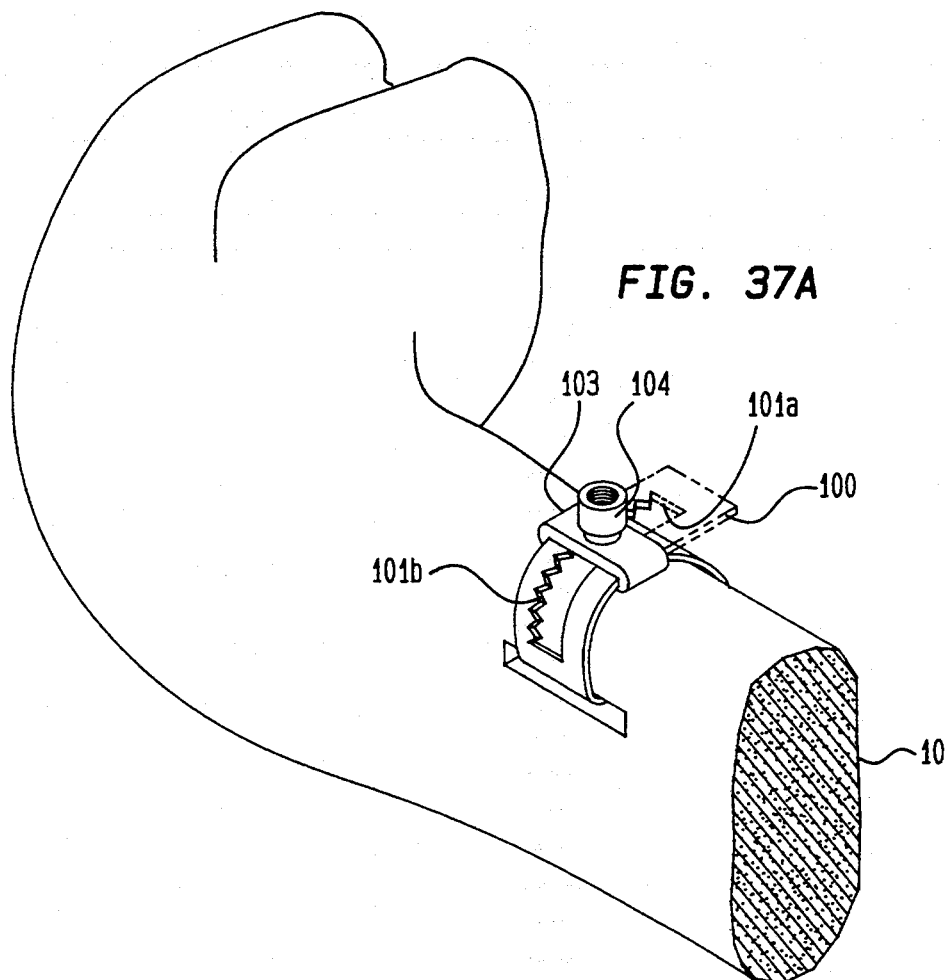
FIGS. 37A, 37B and 37C illustrate a technique according to the present invention for employing a clamp on the jawbone to support a prosthesis and for drilling a vertical incision in the jaw.
Figure 37B:
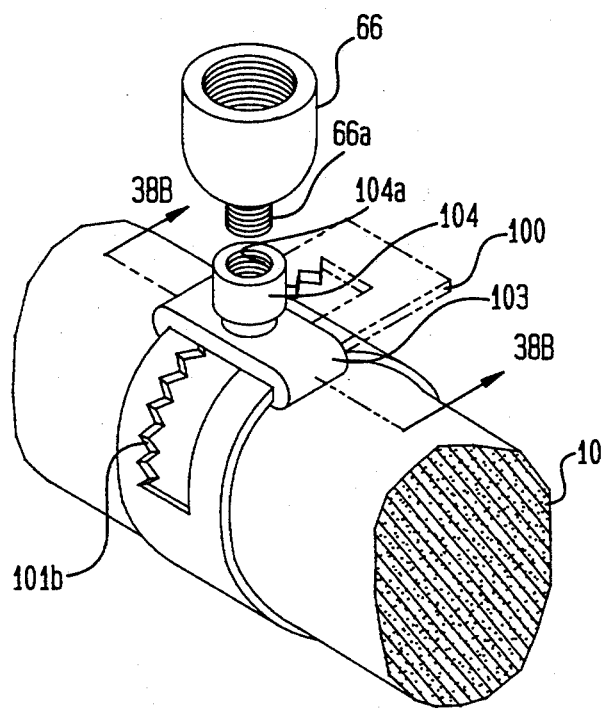
Figure 37C:
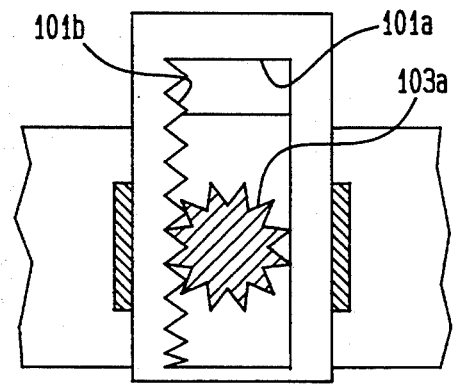

In cases in which the jawbone has been found to be too fragile for drilling, a clamp 100 is employed in accordance with the present invention to fit over the upper surface of the jaw 10 as shown in FIGS. 37A–37C. The clamp 100 shown in FIG. 37A is formed of a strip of readily bendable biocompatible, malleable metal, such as titanium or titanium alloy which is adapted to conform to the shape around the upper surface of the jaw 10. Centered along the length of the upper portion of the clamp 100, extending several inches along the length, is a rectangular cut 101a, along one of the long edges of which are a series of gear teeth 101b.

A metal strap 103 fits transversely across strip 100 and engages the edges thereof, slideably, and has interposed at its center an internally screw-threaded receptacle 104 which terminates in an axially extending rotatable toothed wheel 103a which engages the gear teeth 101b in progression.

The internal screw threads 104a are designed to accommodate the screw-threaded projection 66a from the base of the support member 66, holding it in place on 104 which represents a healing collar.

Thus, the position of the support 66 can be fixed as desired on the jaw 10, so that a position can be selected for securing a prosthesis on the jaw.

FIGS. 37B and 37C show a technique developed in accordance with the present invention for using a clamp on the jaw to support a prosthesis instead of drilling an incision in the jaw.

A further advantage of the present invention resides in the method of preparation of the soft tissue 110 and jawbone 10 for a dental implant. This method may be used for both vertical 3 and horizontal 6 implants or a combination of both such as previously described.

Figure 38A:
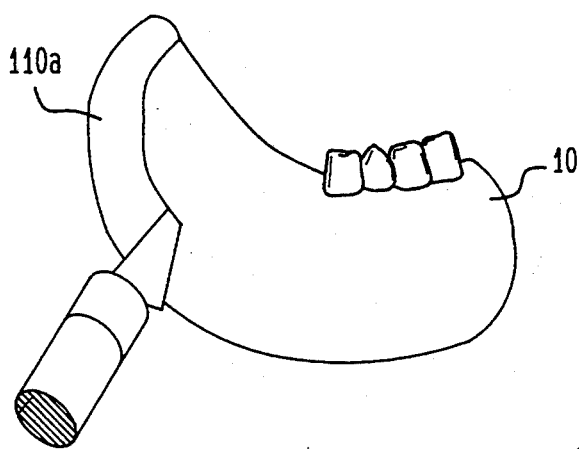
FIG. 38A illustrates another approach to installing a substitute tooth beginning with the making of an incision with a knife from the top of the jawbone.

FIG. 38A shows a unique approach to installing the substitute tooth by making an incision 110a from along the lateral border of the jaw. The prior art method for a vertical implant involves an incision along the crest of the ridge and healing of the tissue around the healing collar which is often fibrous and not uniform.

Figure 38B:
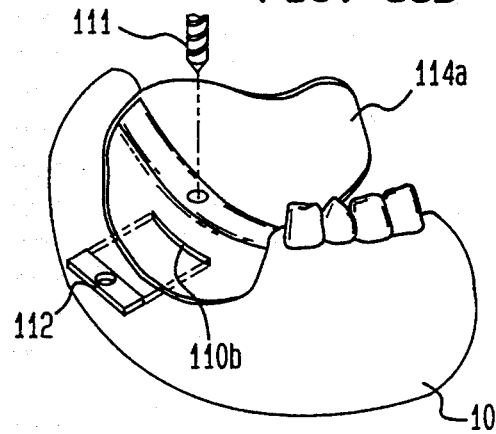
FIG. 38B illustrates a drill entering the jawbone after a flap of gum has been cut back and removed to expose the upper bony ridge of the jawbone.

FIG. 38B shows the drill 111 being interposed from the top of the jaw, with the lower plate 112 being placed in the cut 110b after a flap of gum 114a has been pulled back.

Figure 38C:
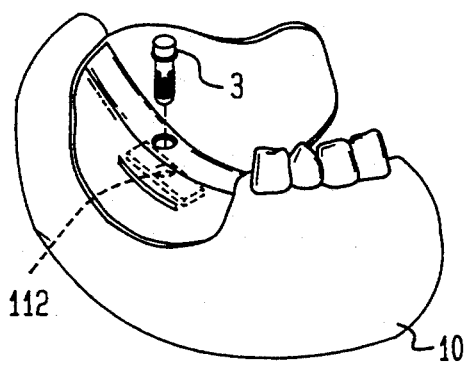
FIG. 38C illustrates the use of a vertical post being attached to a horizontal anchor plate from the top of the exposed jawbone.

FIG. 38C illustrates a vertical support post or sleeve 3 being screwed into the horizontal anchor plate 112 through the hole made by the drill 111 in FIG. 38B.

Another embodiment of the invention resides in the use of a cutting device 113 having a central pin that fits into the center of a healing collar and acts as a guide for the cutting device 113 in order to remove a plug of tissue 114b around the healing collar, thereby exposing the healing collar in a rapid and clean fashion. This feature may be more fully understood by reference to FIGS. 38D, 38E, 38F, 38G, and 38J as set forth below.

Figure 38D:
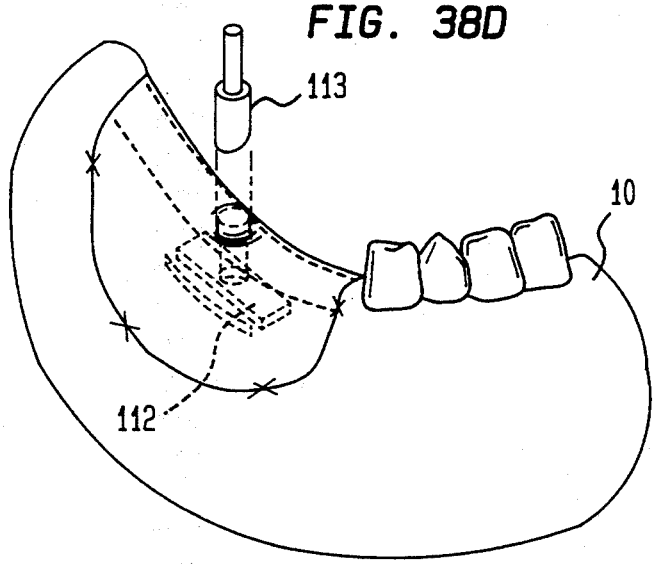
FIG. 38D illustrates a surgical incision made with a cutter device down to the horizontal incision made in the jawbone guided by an internal pin in the cutter device contacting the top of the vertical post.

FIG. 38D shows the cutter device 113 drilling down from the top of the jaw 10 toward the lower plate 112 which is in place in the surgical cut 110 after the flap 114a has been sutured back to the gum.

Figure 38E:
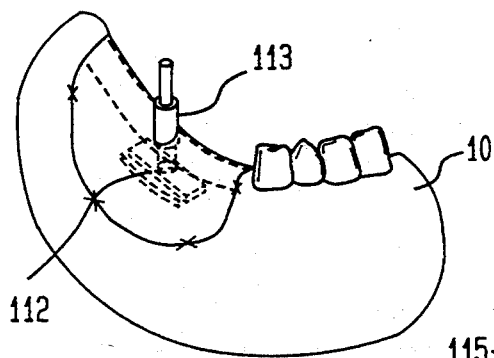
FIG. 38E illustrates the cylindrical cutter device rotated to cut a portion of the gum from the top of the exposed jaw.

FIG. 38E shows the cylindrical cutting device 113 in operation on the top of the jaw 10.

Figure 38F:
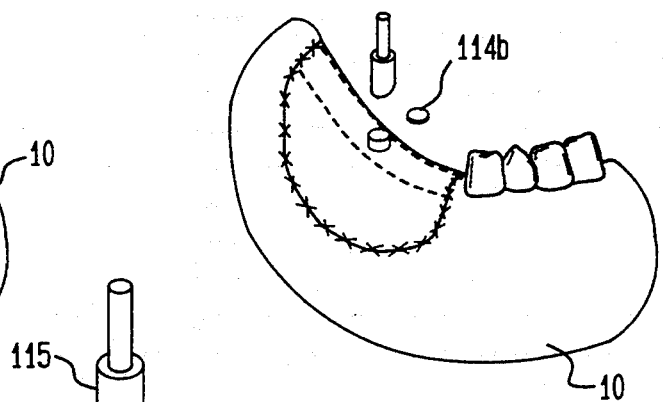
FIG. 38F illustrates the cylindrical cutting device after it has operated on the top of the jaw and has actually incised a small cylindrical plug of gum.

FIG. 38F shows the cylindrical cutting device after it has operated on the top of the jaw 10 and has actually incised a small cylindrical piece of gum 114b.

Figure 38G:
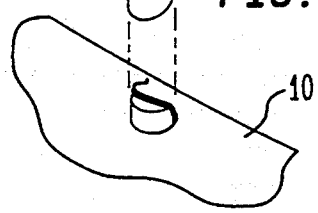
FIG. 38G illustrates a cylindrical cutting device having a spiral edge being applied to the top of the patient's jawbone.

FIG. 38G shows a cylindrical cutter device being applied to the top of the patient's jaw 10 in which the lower blade of the cylindrical cutter is shaped in the form of a spiral.

Figure 38H:
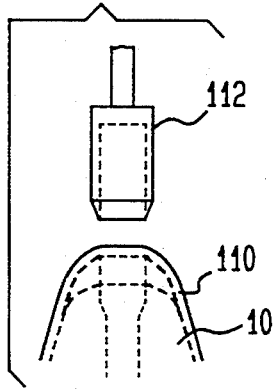
FIGS. 38H and 38I illustrate prior art cylindrical cutting devices showing the manner in which a small cylindrical segment has been cut off between the implant and gum.
Figure 38I:
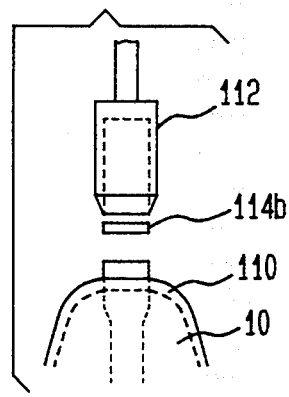

FIGS. 38H and 38I show cylindrical cutters 112b of prior art form in which a small cylindrical segment 114b has been cut off between the implant and the gum.

Figure 38J:
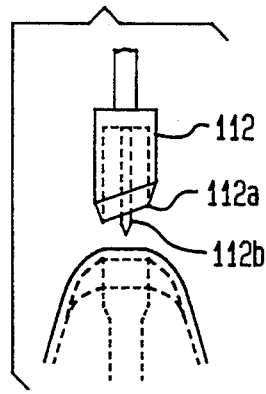
FIG. 38J illustrates the modification according to the present invention of the device is illustrated in FIGS. 38H and 38I, in which the cutting edge of the cutting device is beveled.

FIG. 38J shows a modification of the devices of FIG. 38G and 38H, in which the cutting edge 112a of the cutting device is bevelled. Guide pin 112b contacts the top of vertical post 3 which holds it in rotational position during cutting.

The procedure illustrated in FIGS. 38A–38J should be sufficient to anchor a vertical post 3 to an anchor plate 112 in a jawbone 10. The holding power can be enhanced, however, by other techniques such as using screws to hold the apparatus in position.

Figure 39A:
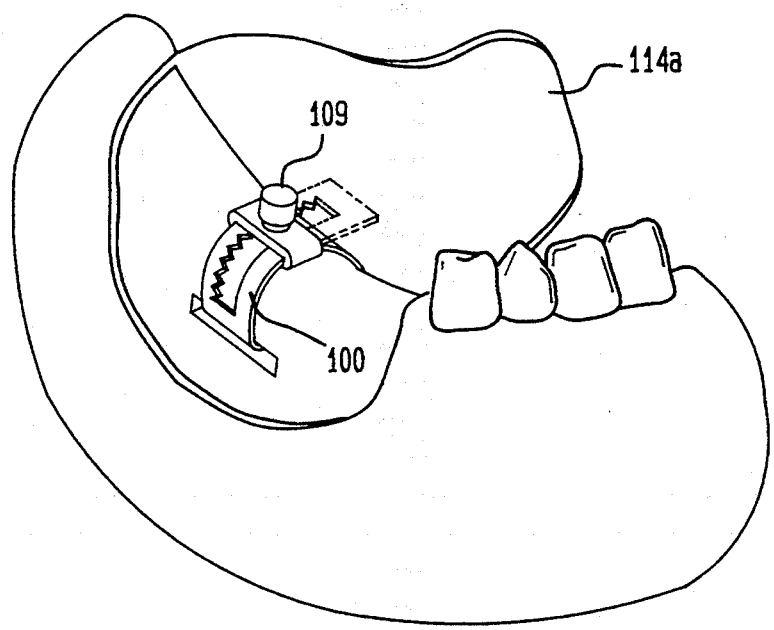
FIG. 39A illustrates the use of a clamp to hold a healing collar with a cutting edge between the gum and the bone, after the flap of gum has been drawn back.

FIG. 39A shows the use of a clamp 100 between the gum 110 and the bone 10 at the top of the jaw after an incision has been made.

Figure 39B:
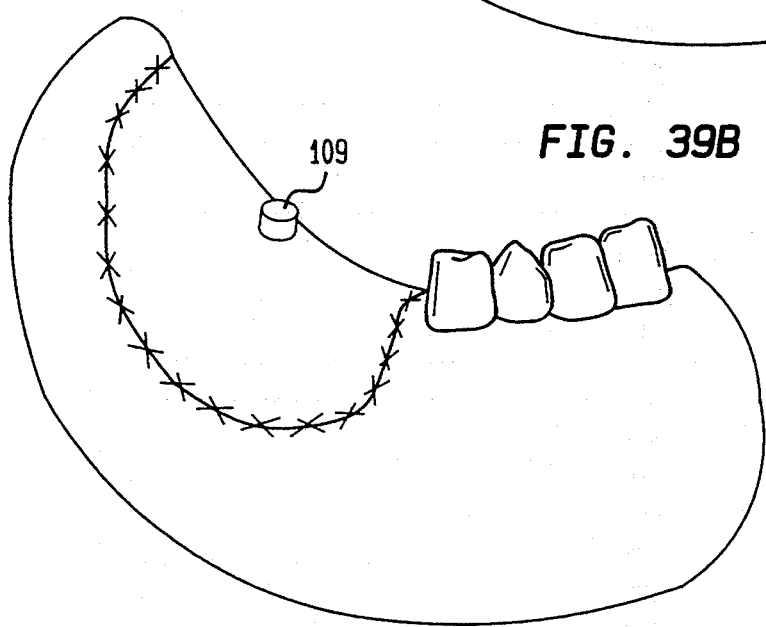
FIG. 39B illustrates the apparatus of FIG. 39A with the flap of gum replaced and sutured into position.

FIG. 39B shows the bone emplacement 109 in place in the jaw after the flap 114a has been sutured back.

The preferred embodiment of the invention comprises a dental implant and stresses more specifically the use of a healing collar 116 having a means for expansion so as to form a coronal prosthesis or attachment for a coronal prosthesis that eliminates the need for the use of screws to affix such coronal prostheses to the internally threaded shaft of an endosseous dental implant.

Prior art surgical screws on healing collars are known in the art and are frequently made of non-corrosive, safe material such as titanium. However, the use is severely limited by the fact that they have to be acquired in the correct size for the proper procedures and are not as versatile as the ones described in the preferred embodiment that follows.

Figure 40A:
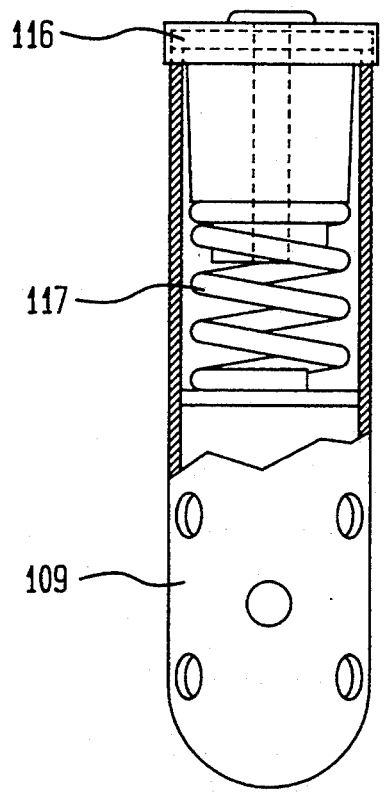
FIG. 40A illustrates in a partial cross-sectional view, a cylindrical healing collar in the vertical plane set in an implant having apertures therein and including a spring that acts as a shock absorber.

FIG. 40A shows a cross-section view of a cylindrical healing collar 116 in a plane vertical to the plane of the gum 110. the implant 109 is located inside the lower inside tip of the healing collar 116. A coil spring 117 depends internally from the collar 116 around the top of the cylinder, which is shown internally in FIG. 40A.

Figure 40B:
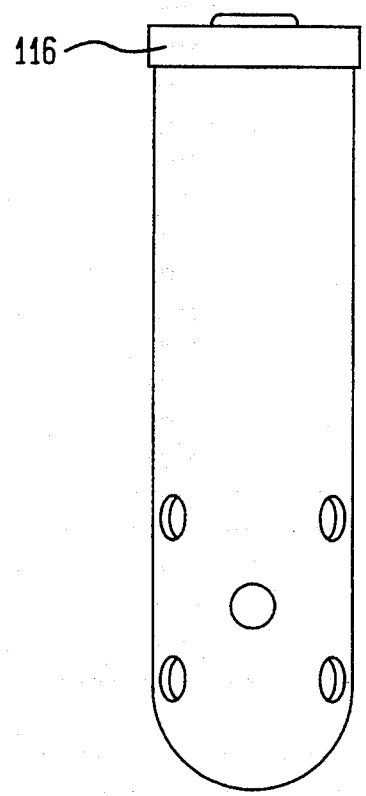
FIG. 40B is a vertical, external view of the implant illustrated in FIG. 40A.

FIG. 40B is an external view of the healing collar 116 and implant 109 of FIG. 40A.

Figure 40C:
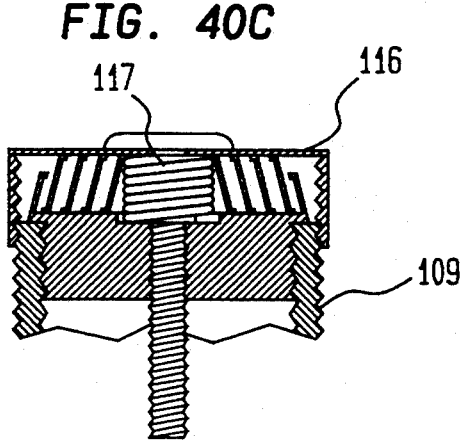
FIGS. 40C and 40D are vertical cross-sectional illustrations of a healing collar shown in its collapsed mode in FIG. 40C and in its expanded mode in FIG. 40D.
Figure 40D:
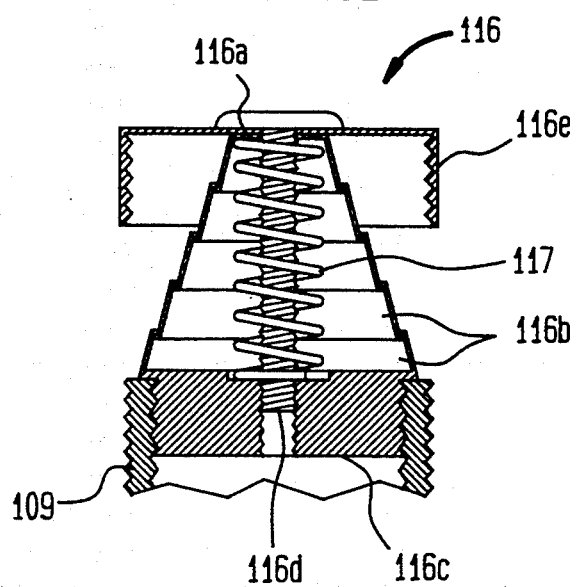
Figure 40E:
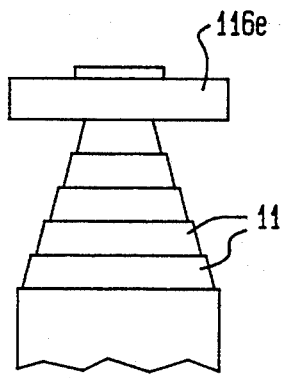
FIG. 40E is an external, cross-sectional view of an implant having a healing collar on the top thereof, such as illustrated in FIG. 40D.

FIGS. 40C and 40D show in detailed sectional views the axial spring 114 of the healing collar 116 collapsed around the implant 109 in FIG. 40C and expanded in FIG. 40D. FIG. 40E is an external view of the healing collar 116 expanded as shown in FIG. 40D.

The healing collar assembly 116 comprises a spring-loaded orifice and top plate 116a, a plurality of interlocking, frustro-conical sections 116b, a base 116c, a cap 116e and threaded post 116d for connecting the cap 116e and orifice top plate 116a to the base 116c in the top of implant 109.

Figure 40G:
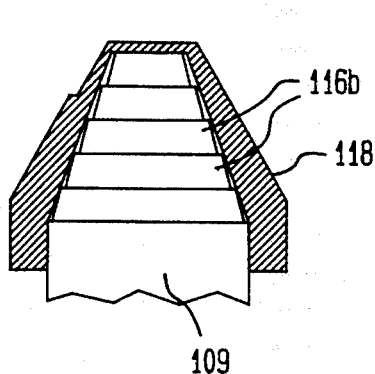
FIG. 40G illustrates an externally applied plastic or metal cap or coping which fits precisely over the spring-biased healing collar illustrated in FIGS. 40C, 40D or 40E.
Figure 40H:
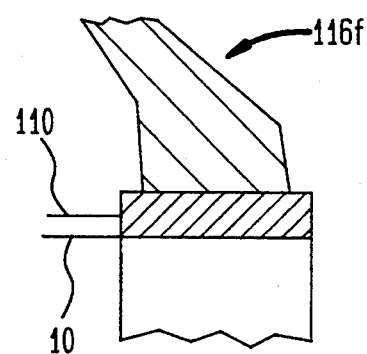
FIG. 40H illustrates a tiltable embodiment of the expandable healing collar such as illustrated in FIGS. 40C–40G.
Figure 40F:
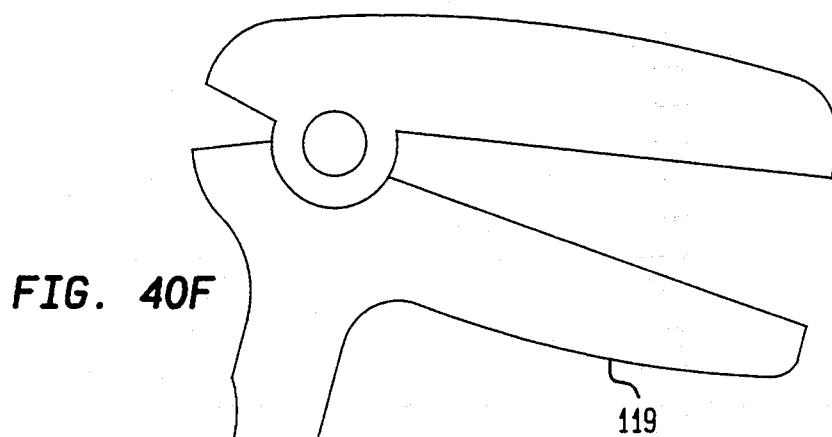
FIG. 40F illustrates a prior art compressing device which terminates in a nub which is applied by a hand-operated syringe to express a filler into the expanded healing collar such as illustrated in FIGS. 40C–40G.

FIG. 40F shows a prior art compressing device 119 terminating in a nub 120 which is applied by a hand-operated clamp to the orifice 116a at the top of a spring 117 mounted on a healing collar 116. Internally surrounding the spring 117 in FIG. 40F is a compressible flexible material 116f, which when the prior art clamp is compressed, comprising the spring, bringing pressure on the top of the healing collar 116, thereby forcing material 116f inside.

The compressible, flexible material 116f may be a thermoplastic and/or epoxy-like material in nature or self-curing or light curable and being of a rigid or semi-rigid nature upon setting after insertion by compressing device 119 into the expandable healing collar 116. Materials are available on the market that might be suitable for such purpose. Such materials are available, for example, through Darby Dental Supply Co., Inc., 3890 Park Central Boulevard North, Pompano Beach, Fla. 33064.

FIG. 40G shows externally an elastomeric cap 118 which fits over the spring-biased top shown in FIGS. 40C, 40D and 40E.

Efforts have been made in the prior art to deal with the problem of coronal prostheses that are not truly vertical to the gum line. Prior art approaches have been fairly complicated and expensive. Note, for example, the tiltable, adjustable insert for dental implant described in U.S. Pat. No. 5,071,350 which requires a ball and collar arrangement in order to produce a tiltable, rotatable, adjustable prosthesis connector. Devices such as that can be acquired, for example, from Universal Prosthetics, 15821 Ventura Boulevard, Suite 420, Encino, Calif. 91436. However, an easier, and less expensive, approach is described below.

FIG. 40H illustrates an alternative embodiment 116f of the expandable healing collar 116 in which the frustro-conical sections are nested in such a way as to tilt the filled healing collar 116f so as to accommodate a crown that is mounted at an angle with respect to the gum line 110.

The preferred embodiment of the expandible healing collar 116 includes a plurality of interlocking, frustroconical sections 116b as shown in FIG. 40E. It is possible, however, to provide for expandability by other means. For example, instead of using interlocking, frustro-conical sections like 116b, it would also be possible to have pleated sides which can expand or collapse or use a balloon-like structure. The important characteristic is that the healing collar structure be capable of expanding and collapsing in a manner consistent with the teachings of this invention.

Figure 40I:
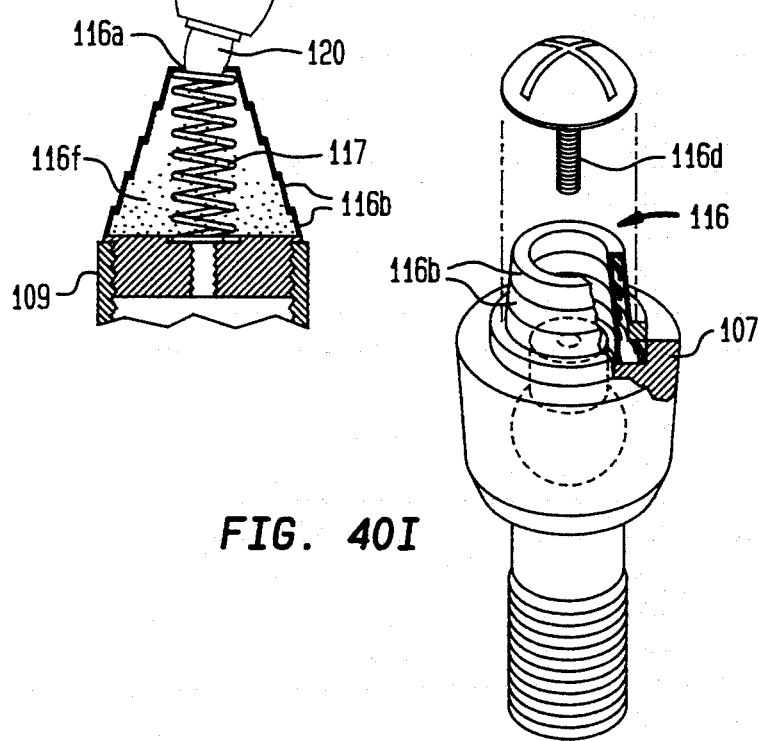
FIG. 40I is a partially exploded, cross-sectional view of a healing collar in its expanded mode with a screw shown in relative alignment above the healing collar and vertical post.
Figure 40J:
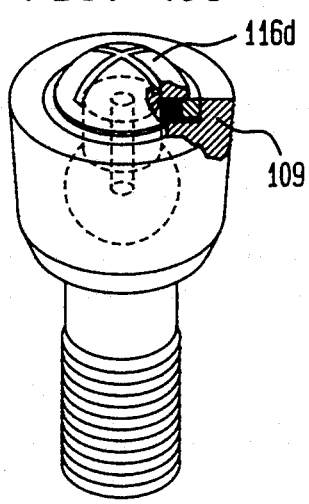
FIG. 40J illustrates the healing collar and post of FIG. 40I after the screw has been screwed down, thereby collapsing the healing collar into the vertical post.

FIG. 40I illustrates the manner in which a threaded post in the form of a screw 116d is aligned above an expanded healing collar 116 formed of sections 116b above implant 109. When screw 116d is rotated clockwise, it advances into the post 109 thereby collapsing the healing collar 116 into the cavity in the top of the post 109.

Figure 41A:
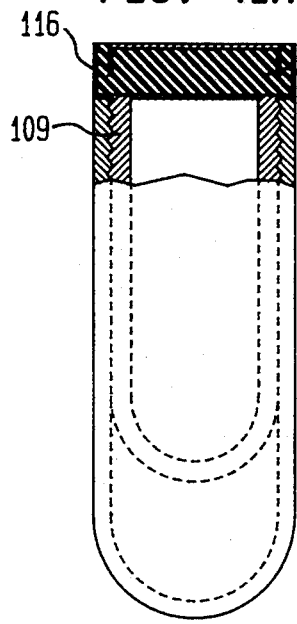
FIGS. 41A through 41E illustrate in partial cross-sectional views, an implant including a flat, shock absorbing rubber-like cap located on the top of the cylindrical insert.
Figure 41B:
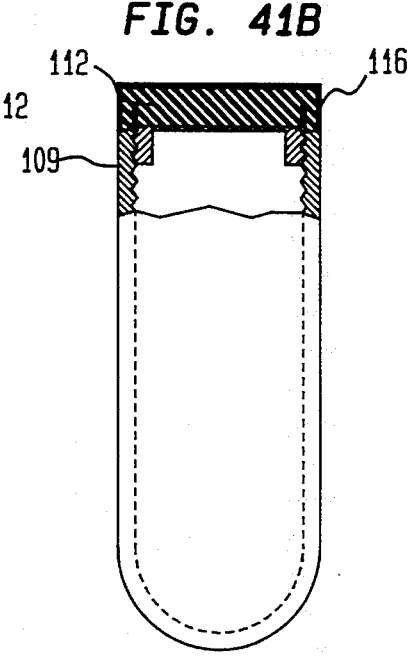
Figure 41C:
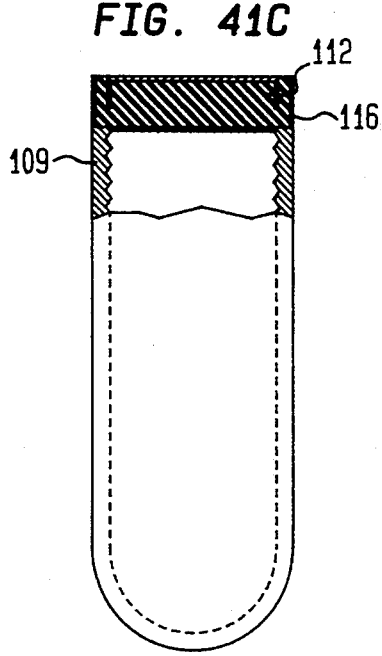

FIGS. 41A through 41D show in section a healing collar in which a flat rubber cap 121 is applied across the top covering the cylindrical insert which extends into the collar internally in vertical telescopic relation to the healing cylinder. The insert may extend to different depths in the enclosing healing sleeve as shown in FIGS. 41A, 41B or 41C.

Figure 41D:
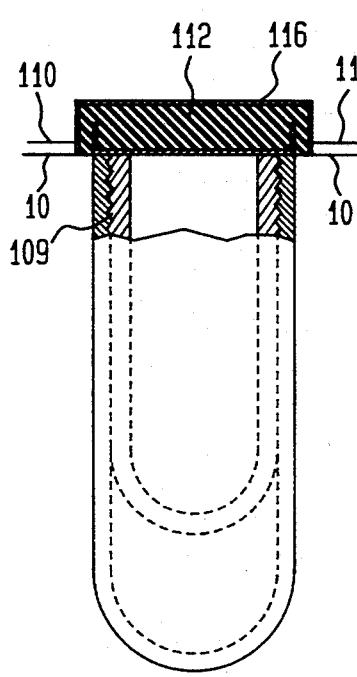
Figure 41E:
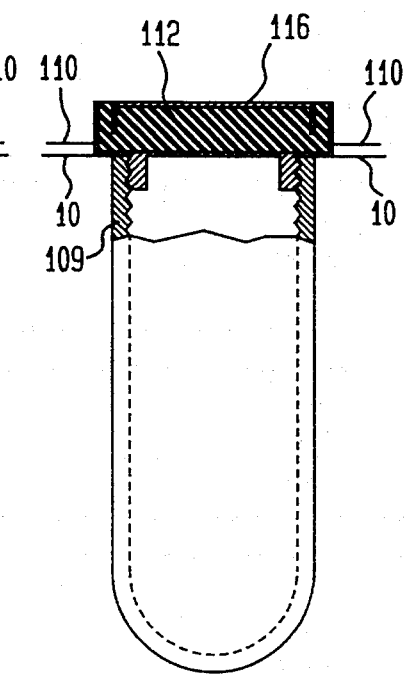
Figure 41F:
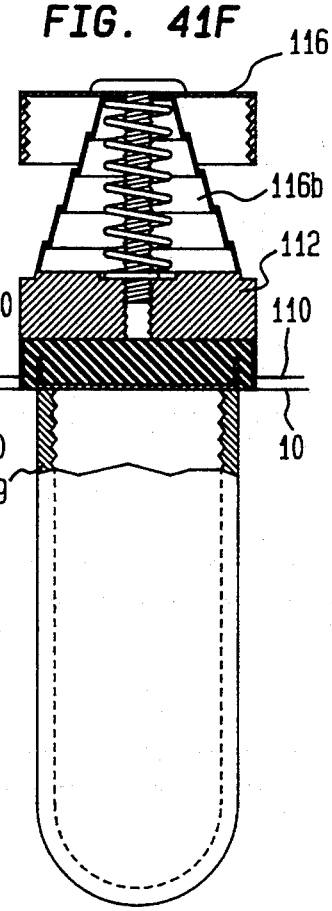
FIG. 41F illustrates the implant including the rubber-like cap with an expandable healing collar expanded and in place on top.

FIGS. 41D, 41E and 41F show the relationship between the gum line 110 and the bone line 10 when the healing collar 116 having a rubber cap 112 has been inserted into the jaw 10. In particular, FIG. 41 shows the expandable healing collar 116 in position above rubber cap 112.

Another embodiment of the invention described in FIGS. 42A-42E allows for the removal of an inner core which is threadably received in an outer core when the threaded internal portion which carries the coronal prosthesis is defective.

Figure 42A:
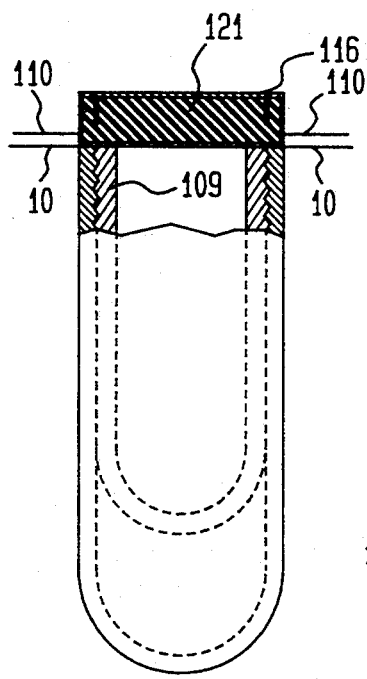
FIG. 42A illustrates in a partial cross-sectional view the healing collar with an elastomer or rubber-like cap in place in the jawbone.

FIG. 42A shows in section, the healing cylinder or cap 116 with the elastomer or rubber cap 121 in place in the jaw 10.

Figure 42B:
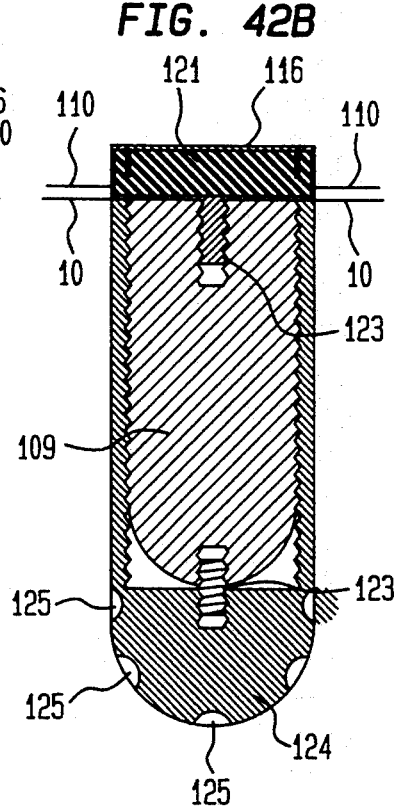
FIG. 42B illustrates the cylindrical implant in full vertical cross-sectional view in place in the jaw and held into position with internal screw threads so that the core can be removed.

FIG. 42B shows the cylindrical implant 122 in section in place in the jaw 10, held in place by screws 123 at the top and at the bottom 124 which is semi-spherical in form with a plurality of openings 125 at the lower end to allow contact with the bone 10.

Figure 42C:
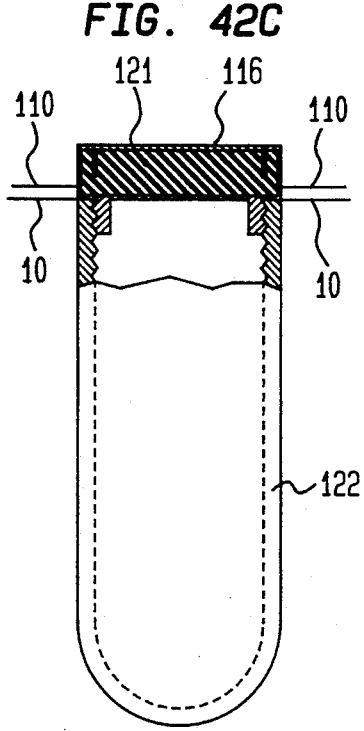
FIGS. 42C, 42D and 42E are partial cross-sectional views showing the implant in place in the bone with the rubber or elastomer cap in place across the top.
Figure 42D:
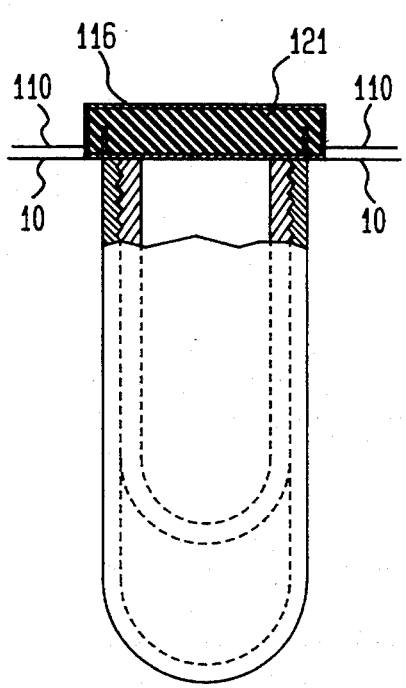
Figure 42E:
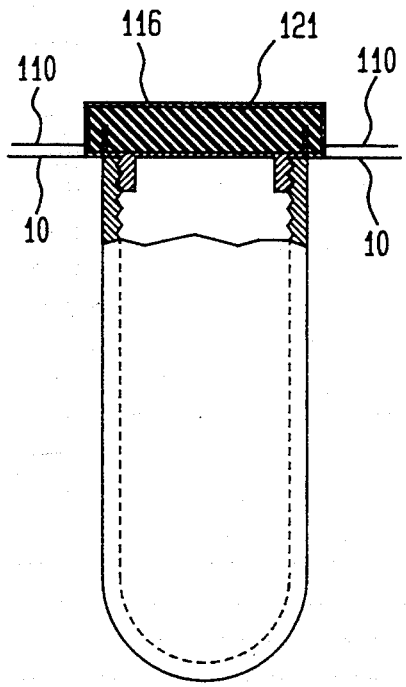

FIGS. 42C, 42D and 42E are cross-sectional views of the implant 122 in place in the bone 10 with the rubber or elastomer cover 121 in place across the top of the gum 110.

Figure 43A:
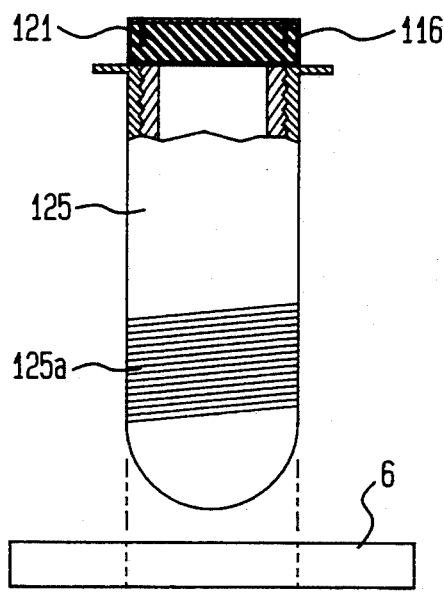
FIGS. 43A and 43B illustrate in partial cross-sectional views a modification of the implant wherein the threaded exterior body of the implant is received into a horizontal anchor plate.
Figure 43B:
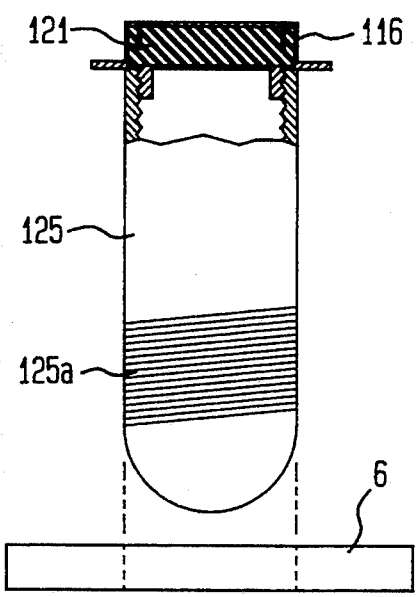

FIGS. 43A and 43B show in partial cross-sectional views modifications of the implant 125 with the healing cylinder or cap 116 in place in which the external wall of the outer cylinder 125 is screw-threaded with threads 125a to be screwed into place in the top of the jaw and received in plate 6.

Figure 44A:
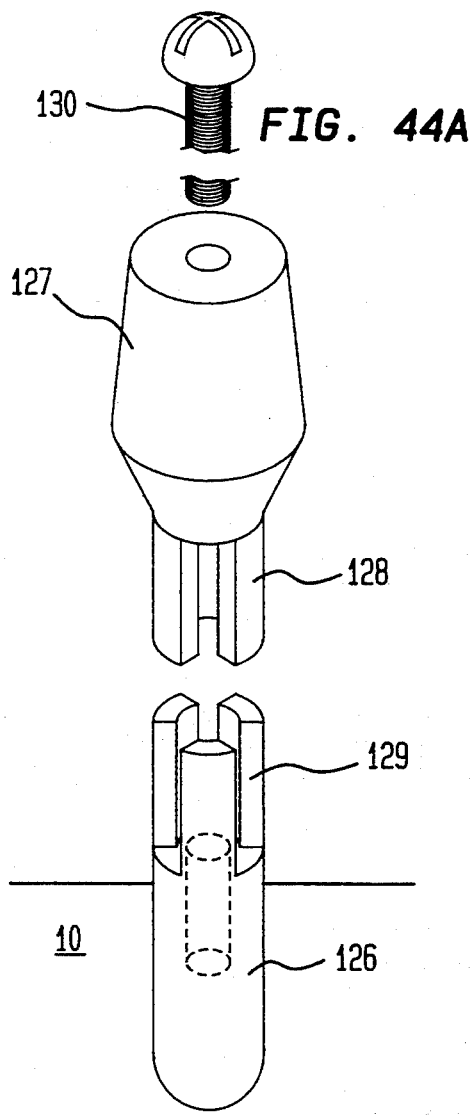
FIGS. 44A and 44B show modifications of the healing collar such as illustrated in FIGS. 42A et seq., in which the base of the healing collar comprises a hex male/female structure having three legs which are received respectively in three vertical grooves in the vertical implant employed to attach the prosthesis to said vertical post and a screw to keep the structure in place.

FIG. 44A is a modification of the healing collar 116 shown in FIGS. 42A-43B in which the implant 126 in place in the jaw 10 is topped by a device 127 in the form of a frustro-conical member which terminates at its bottom end in a key 128 which is constructed to fit into the keyhole 129 of the implant 126. A screw 130 holds the assembly in place.

Figure 44B:
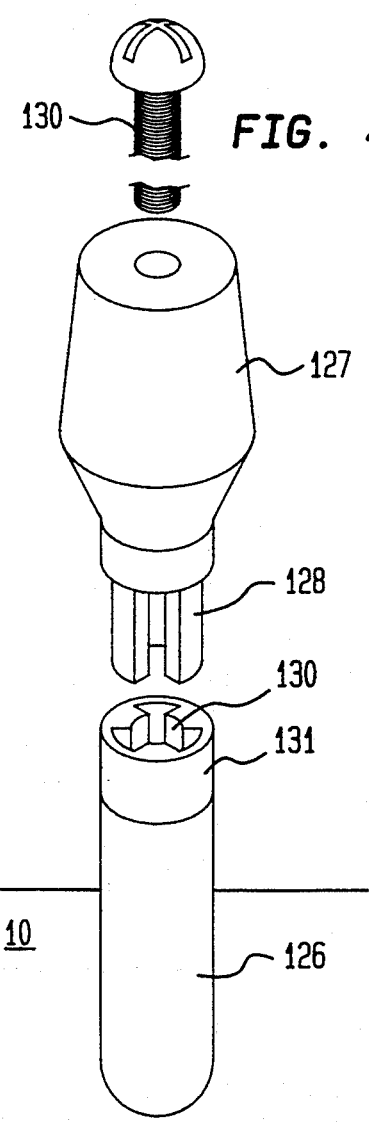

FIG. 44B is a modification of the embodiment of FIG. 44A where the key 128 fits into a special keyhole 130 in modified healing collar 131.

Figure 44C:
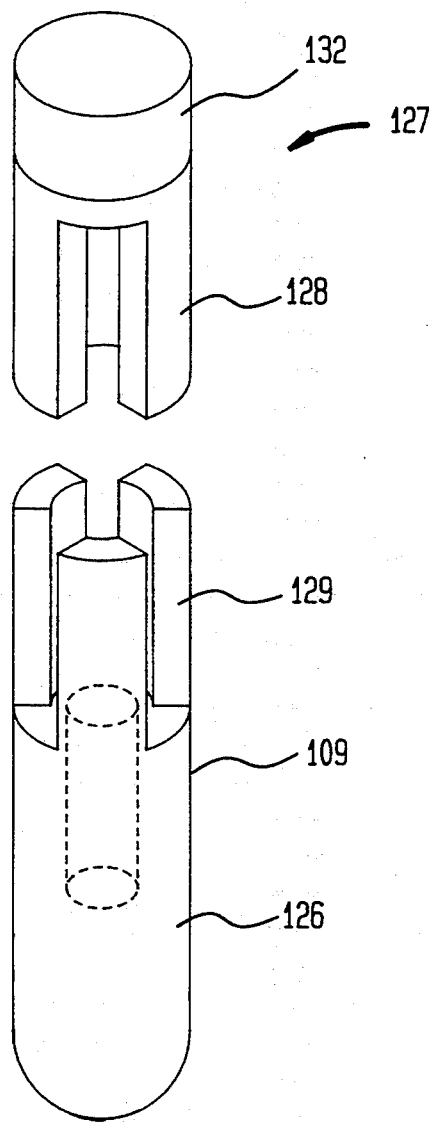
FIG. 44C illustrates an alternative embodiment of the versions illustrated in FIGS. 44A and 44B with an expandable healing collar in which the base of the healing collar comprises a hex male/female structure having three legs which are received, respectively, in three vertical grooves in the vertical implant employed to attach the prosthesis to the vertical post which is held in place by a screw once the expandable healing collar is activated.

FIG. 44C shows a modified healing collar 132 terminating at its lower end 128 in a female/male hex which is shaped to fit into and lock in place with the key 129 of implant 126.

Another embodiment of invention provides for the use of an expandable healing collar with a thread and/or screw which can be affixed to a previously endontically treated tooth, whereby the expandable healing collar is affixed to the canal of the root of a tooth and filled so as to restore the broken coronal portion of the tooth. The embodiment calls for the use of a tapered and at least partially threaded and split vertical post. While the use of split, threaded vertical posts in known in the prior art, the use of the combination of a tapered split vertical post, especially one wherein the threads are not continuous around the sides and further in combination with an expandable healing collar is not known or used.

One of the concerns with prior art implants is that there is a tendency to rotate. In order to minimize that factor, certain prior art implants include an internal hex to provide a stronger, more precision-like fit. See, for example, the Spectra System TM implants made by Cor-Vent of Encino, Calif. which includes an internal hex configuration or the IMZ TM implants made by Interpore which include an external hex configuration. A significant improvement over that structure is described in FIGS. 44A–44C which provide for a split male/female hex-like configuration which has superior anti-rotational factors and, in addition, allows the use of a wider screw so as to reduce the incidence of fracture to the screw.

Figure 44D:
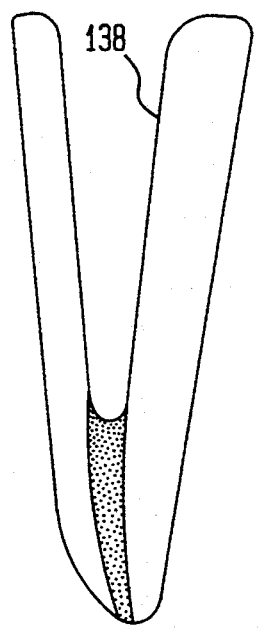
FIG. 44D illustrates an incision in the jawbone and tooth such as might take place during a root canal procedure.
Figure 44E:
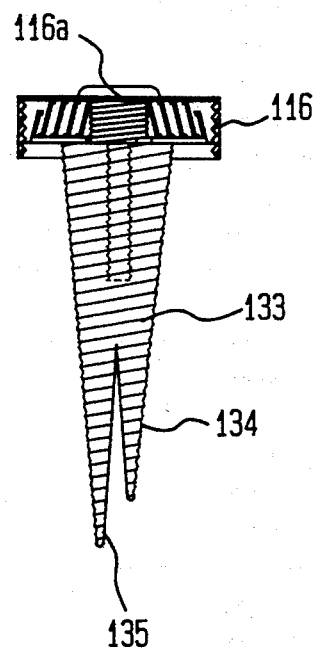
FIG. 44E illustrates another embodiment of the invention in which the expansible healing collar is located on top of a tapered, threaded, split vertical post.

FIGS. 44D through 44H describe an alternative embodiment of the invention in which the vertical implant post 133 is split and includes threads 134. The tapered vertical post 133 is adapted to fit in the cavity 138 left after a root canal such as illustrated in FIG. 44D. The vertical implant post 133 includes a slot 135 at the bottom so that it can wedge into the tapered cavity of a root canal opening 138. Threads 134 preferably completely surround the tapered vertical post 133 as shown in FIG. 44E. The tapered post 133 is preferably capped with an expandable healing collar 116.

Figure 44F:
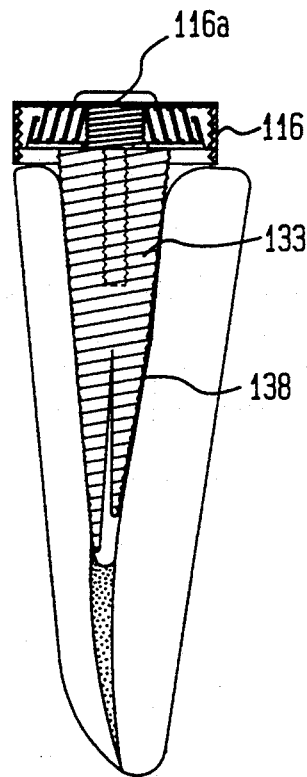
FIG. 44F illustrates the embodiment of split, tapered, threaded post embodiment of FIG. 44E in position in the root canal.
Figure 44G:
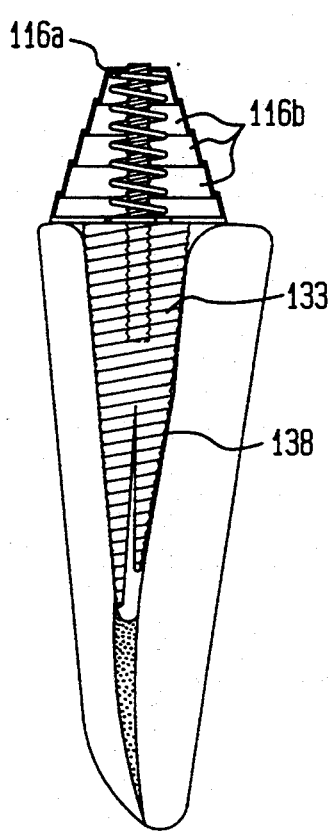
FIG. 44G illustrates the tapered, split, threaded post embodiment of FIG. 44E with the healing collar expanded.
Figure 44H:
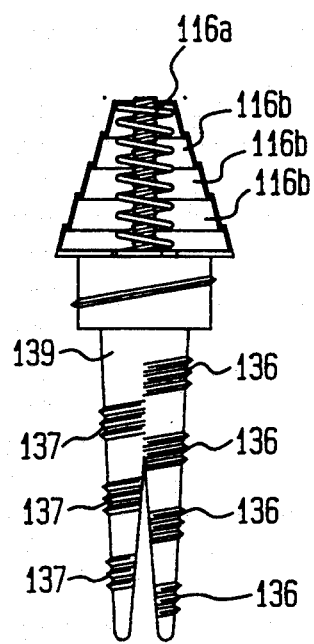
FIG. 44H illustrates an alternative embodiment of the tapered split vertical post of FIGS. 44E–44G showing the threads on alternate opposite sides of the split vertical post.

FIG. 44F illustrates the tapered, threaded implant 133 in position in a root canal cavity 138 prior to expansion of the healing collar 116. FIG. 44G illustrates the tapered, threaded vertical implant 133 shown in FIG. 44F with the healing collar assembly 116 expanded according to the method previously described. FIG. 44H is an alternative embodiment 139 of the tapered implant 133 in which alternate sides of the split, tapered implant include threads. As shown in FIG. 44H, one side of the split, tapered vertical implant includes threads 136 across from which there is no threaded area. Similarly, the other side of the tapered, split vertical implant 139 includes threaded sections 137 which correspond and line up across from non-threaded sections on the opposite side. In other words, the threaded sections 136 and 137 are alternately located on opposite sides of the split portions of the vertical tapered threaded implant 139.

While the invention has been described with reference to a preferred embodiment, it will be understood by those of ordinary skill in the art that various changes in structure and function can be made without departing from the spirit and scope of the invention as a whole.

I claim:

1. A dental apparatus for attachment to a vertical post which passes through the gums and is attached to the jawbone, said apparatus comprising:
    a base attachable to a first end of said vertical post;
    an expandable means attachable to said base for defining an interior cavity with respect to said base; and,
    an orifice means in said expandable means for passing filler into said interior cavity through said orifice to expand said expandable means.

2. The apparatus of claim 1 wherein said expandable means comprises an expandable healing collar which includes a plurality of nested, concentric, conical sections which form a frustro-conical shape when said expandable means is expanded by said filler means.

3. The apparatus of claim 2 further comprising:
    screw means located inside of said interior cavity to assist in the expansion of said expansion means.

4. The apparatus of claim 3 further comprising:
    spring means located inside of said interior cavity to assist in the expansion of said expansion means.

5. The apparatus of claim 4 wherein said vertical post is integrally attached to said base.

6. The apparatus of claim 4 wherein said vertical post includes a threaded means at a first end for attachment to said base.

7. The apparatus of claim 6 further comprising:
    an anchor plate locatable in a cavity inside of said jawbone and attachable to a second end of said vertical post opposite from said first end attached to said base.

8. The apparatus of claim 7 further comprising:
    threaded means for attaching said second end of said vertical post to said anchor plate.

9. The apparatus of claim 8 wherein said anchor plate is expandable to expand to substantially the size of said cavity in said jaw.

10. The apparatus of claim 9 wherein said anchor plate includes a first and a second section connected together by a rotatable threaded means,
    whereby rotation of said rotatable threaded means moves said first and second sections with respect to each other to fill up said cavity in said jaw.

11. The apparatus of claim 9 wherein said anchor plate includes spring-loaded means for automatically filling up said cavity in said jaw.

12. The apparatus of claim 9 wherein said cavity in said jaw is formed by a drill having a head with a cutting surface on its periphery and wherein the diameter of said cutting head is greater than the diameter of the shaft of said drill.

13. The apparatus of claim 12 further comprising:
    a sleeve for surrounding said vertical post,
    wherein said vertical post includes a plurality of vertical slits so that when passed through a first end of said sleeve it compresses and when it emerges from the other second end of said sleeve, it expands to fill up the cavity formed by said cutting head of said drill.

14. The apparatus of claim 9 wherein said anchor plate includes a plurality of flexible spring-like means which impinge outwardly against the walls of said cavity.

15. The apparatus of claim 8 wherein said filler means comprises a rigid material.

16. The apparatus of claim 8 wherein said filler means comprises a semi-rigid material.

17. The apparatus of claim 8 wherein said filler means comprises a material taken from the group of:
    epoxy, thermoplastic, glass ionomers or cement-like fillers.

18. The apparatus of claim 8 wherein said filler means comprises a light curable material.

19. The apparatus of claim 8 further comprising:
    a crown attachable to said expandable means.

20. The apparatus of claim 7 wherein said anchor plate include means to attach at least two vertical posts to said anchor plate.

21. The apparatus of claim 7 wherein said anchor plate is attached substantially perpendicular to said vertical post.

22. The apparatus of claim 7 wherein said anchor plate forms an oblique angle with respect to said vertical post when attached to said vertical post.

23. The apparatus of claim 7 further comprising:

template means locatable in said cavity inside of said jawbone and also locatable above said jawbone for guiding a drill through said jawbone,
wherein a hole is formed in said jawbone properly aligned for receiving said vertical post.

24. The apparatus of claim 23 wherein said template means comprises a three-sided template including:
a top plate locatable above said jawbone and having a first aperture therein;
a bottom plate locatable in the interior cavity in said jawbone and having a second aperture therein; and,
a bridge section connected said top and bottom plates for keeping said top and bottom plates in parallel relationship with respect to each other,
wherein a drill can pass through said first aperture in said top plate and through said second aperture in said bottom plate, thereby aligning the vertical post hole properly with respect to said jawbone.

25. The apparatus of claim 6 wherein said vertical post comprises a sleeve and wherein said sleeve includes a vertical slit therein to accommodate expansion of said sleeve.

26. The apparatus of claim 25 further comprising:
an internal screw accommodated telescopically in said sleeve for expanding said sleeve by expanding said vertical slit in said sleeve.

27. The apparatus of claim 4 further comprising:
tiltable means incorporated in said expandable healing collar for tilting said expandable healing collar with respect to said vertical post.

28. The apparatus of claim 2 further comprising:
shock absorbing means located between said vertical post and said healing collar, said shock absorbing means comprising a spring.

29. The apparatus of claim 2 wherein said vertical post comprises an inner sleeve threadably received within an outer sleeve and wherein said healing collar is attached to said inner sleeve,
whereby rotation of said inner sleeve permits said healing collar and inner sleeve to be removed from said outer sleeve.

30. The apparatus of claim 2 further comprising:
coping means for covering said healing collar when expanded.

31. The apparatus of claim 30 wherein said healing collar may be tilted so that it can receive and accommodate a coronal prosthesis at an angle greater than 0° with respect to the long axis of said vertical implant.

32. The apparatus of claim 1 further comprising:
shock absorbing pad means located between said base and said vertical post for absorbing shock impact imposed upon said expandable means.

33. The apparatus of claim 1 further comprising:
tiltable means to permit said expandable means to tilt with respect to said vertical post.

34. The apparatus of claim 1 wherein said vertical post comprises an inner sleeve and an outer sleeve with a layer of elastomer material interposed internally between said sleeves.

35. The apparatus of claim 1 further comprising:
a clamp mountable on said jawbone for forming a substantially horizontal surface with respect to said jawbone; and,
gear means for locking said clamp in a preselected position,
wherein said expandable means is attachable to said clamp.

36. The apparatus of claim 1 wherein said vertical post comprises:
a tapered vertically split post having threads thereon,
wherein rotation of said split post causes said threads to engage the jawbone in a secure fashion.

37. The apparatus of claim 1 further comprising:
a recombinant granulocyte colony stimulating factor (rG-CSF) applied to said apparatus, whereby the application of said factor assists in promoting healing and preventing infection in said jawbone.

38. The apparatus of claim 1 further comprising:
a hollow tool having a beveled edge and a center pin,
wherein said center pin keeps said hollow tool in alignment with said healing collar and further wherein the beveled edges of said cutting tool cuts a ring in said gum around said healing collar when said hollow tool is rotated to receive a plug of said gum.

39. The apparatus of claim 1 wherein a coronal prosthesis is adapted to mate with said vertical post with a hex-like configuration such that said vertical post includes at least three downwardly depending legs which engage respectively with at least three upwardly depending legs on said vertical post.

40. The apparatus of claim 39 further comprising:
a screw for attaching said coronal prosthesis to said vertical post.

41. The apparatus of claim 1 further comprising a coronal prosthesis which is adapted to engage with a hex-like structure on said vertical post, said coronal prosthesis including at least three downwardly depending legs adapted to engage with at least three slots in the upper portion of said vertical implant.

42. The apparatus of claim 40 further comprising:
a screw for attaching said coronal prosthesis to said vertical implant.

43. The apparatus of claim 1 wherein said expansible means comprises a healing collar and a hex-like structure for engaging said vertical post including at least three downwardly depending legs adapted to engage with three upwardly depending legs forming part of said vertical implant.

44. The apparatus of claim 1 comprising a molly bolt-like structure including:
thread means located in said vertical post; and,
wing means locatable at the end of said vertical post receivable in said incision in said jawbone,
wherein rotation of said threaded means causes said wing means to expand and engage the internal walls of said vertical incision.

45. The apparatus of claim 1 further comprising:
a hollow cutting tool having a beveled edge,
wherein the beveled edge of said cutting tool cuts a ring in said gum around said healing collar when said hollow writing tool is rotated to remove a plug of said gum.

46. The apparatus of claim 1 further comprising:
a clotting factor applied to said apparatus, whereby the application of said factor assists in controlling bleeding from said jawbone.

47. A method for installing a dental implant at a distance from a bony ridge including a vertical post locatable in a jawbone covered with gum tissue, comprising the steps of:
cutting back a flap of said gum to reveal the upper bony ridge of said jawbone;
inserting said vertical post with a healing collar attached into said jawbone;

folding said flap back over said jawbone and said healing collar;

cutting out the area around said healing collar with a hollow tool having a beveled edge and a center pin for keeping said tool in alignment with said healing collar, wherein the beveled edge of said hollow cutting tool cuts a plug in said flap around said healing collar; and, suturing the flap back in position.

48. The method of claim 47 wherein said healing collar comprises an expandable healing collar, said method further comprises the step of:

filling said expandable healing collar with a filler material to expand said healing collar.

49. The method of claim 48 further comprising:

applying a recombinant granulocyte colony stimulating factor (rG-CSF) to said vertical post in order to control bleeding from said jawbone.

* * * * *